United States Patent
Moriwaki et al.

(10) Patent No.: US 10,964,020 B2
(45) Date of Patent: Mar. 30, 2021

(54) SIMILAR CASE IMAGE SEARCH PROGRAM, SIMILAR CASE IMAGE SEARCH APPARATUS, AND SIMILAR CASE IMAGE SEARCH METHOD

(71) Applicant: FUJITSU LIMITED, Kawasaki (JP)

(72) Inventors: Yasutaka Moriwaki, Kawasaki (JP); Masahiko Sugimura, Kawasaki (JP); Susumu Endo, Kawasaki (JP); Hiroaki Takebe, Kawasaki (JP); Takayuki Baba, Kawasaki (JP); Yusuke Uehara, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 119 days.

(21) Appl. No.: 16/291,016

(22) Filed: Mar. 4, 2019

(65) Prior Publication Data
US 2019/0197688 A1 Jun. 27, 2019

Related U.S. Application Data

(63) Continuation of application No. PCT/JP2018/002089, filed on Jan. 24, 2018.

(30) Foreign Application Priority Data

Mar. 10, 2017 (JP) .............................. JP2017-046736

(51) Int. Cl.
*G06T 7/00* (2017.01)
*A61B 6/00* (2006.01)
(Continued)

(52) U.S. Cl.
CPC .............. *G06T 7/0014* (2013.01); *A61B 6/50* (2013.01); *A61B 6/5217* (2013.01);
(Continued)

(58) Field of Classification Search
None
See application file for complete search history.

(56) References Cited

U.S. PATENT DOCUMENTS 5,881,124 A * 3/1999 Giger .................... G06T 7/0012
250/363.04
7,206,462 B1 * 4/2007 Betke .................... G06T 7/0012
378/21
(Continued)

FOREIGN PATENT DOCUMENTS

| JP | 08-320923 | 12/1996 |
|---|---|---|
| JP | 2006-6359 A | 1/2006 |

(Continued)

OTHER PUBLICATIONS

International Search Report with English Translation of Relevant Part and Written Opinion of the International Searching Authority (Form PCT/ISA/210, 220, and 237), mailed in connection with PCT/JP2018/002089 dated Jan. 5, 2018 (10 pages).

(Continued)

*Primary Examiner* — Fayyaz Alam
(74) *Attorney, Agent, or Firm* — Fujitsu Patent Center

(57) ABSTRACT

A similar case image search method performed by a computer, the method includes: extracting a lung field area from a medical image and identifying a contour of the lung field area including a chest wall and a mediastinum; identifying a position at which the chest wall and the mediastinum are internally divided and dividing the lung field area into a central area and a peripheral area based on a shape of the lung field area; counting the number of pixels indicating lesions in each of the divided central area and peripheral area; and identifying a similar case image corresponding to similarity level of the number of pixels indicating lesions by (Continued)

referring to a storage unit that stores the number of pixels indicating lesions in each of the areas.

8 Claims, 21 Drawing Sheets

(51) Int. Cl.
| | |
|---|---|
| *G06T 7/12* | (2017.01) |
| *G06F 16/00* | (2019.01) |
| *G06T 7/11* | (2017.01) |
| *G06T 7/30* | (2017.01) |
| *G06K 9/46* | (2006.01) |
| *G06K 9/62* | (2006.01) |
| *A61B 6/03* | (2006.01) |

(52) U.S. Cl.
CPC ............ *A61B 6/5229* (2013.01); *G06F 16/00* (2019.01); *G06K 9/4619* (2013.01); *G06K 9/6215* (2013.01); *G06T 7/0012* (2013.01); *G06T 7/11* (2017.01); *G06T 7/12* (2017.01); *G06T 7/30* (2017.01); *A61B 6/032* (2013.01); *A61B 6/5235* (2013.01); *G06T 2207/30061* (2013.01); *G06T 2207/30096* (2013.01); *G06T 2207/30242* (2013.01)

(56) References Cited

U.S. PATENT DOCUMENTS

| | | | | |
|---|---|---|---|---|
| 2002/0191827 | A1* | 12/2002 | Armato, III | .......... G06T 7/0012 382/131 |
| 2003/0072480 | A1* | 4/2003 | Tsujii | ...................... G06T 9/005 382/132 |
| 2004/0252870 | A1* | 12/2004 | Reeves | ................. G06T 7/0012 382/128 |
| 2005/0207630 | A1* | 9/2005 | Chan | ...................... A61B 6/583 382/131 |
| 2006/0004282 | A1 | 1/2006 | Oosawa | |
| 2008/0298658 | A1 | 12/2008 | Nakashima et al. | |
| 2014/0072193 | A1 | 3/2014 | Motomura et al. | |
| 2017/0011187 | A1* | 1/2017 | Oosawa | ................. G06F 16/51 |
| 2018/0165305 | A1* | 6/2018 | Wang | ................... G06N 3/0454 |

FOREIGN PATENT DOCUMENTS

| | | |
|---|---|---|
| JP | 2006-181025 A | 7/2006 |
| JP | 2008-200368 A | 9/2008 |
| JP | 2009-90054 A | 4/2009 |
| JP | 2011-118543 A | 6/2011 |
| JP | 2014-85851 A | 5/2014 |
| JP | 2015-136480 A | 7/2015 |
| JP | 2015-203920 A | 11/2015 |
| WO | 2006/011545 A1 | 2/2006 |
| WO | 2013/076927 A1 | 5/2013 |

OTHER PUBLICATIONS

EESR—Extended European Search Report of European Patent Application No. 18763395.3 dated Feb. 17, 2020. **JP2014-085851 cited in the EESR was previously submitted in the IDS filed on Mar. 4, 2019.

Japanese Office Action dated Dec. 8, 2020 for corresponding Japanese Patent Application No. 2017-046736, with English Translation, 8 pages.

* cited by examiner

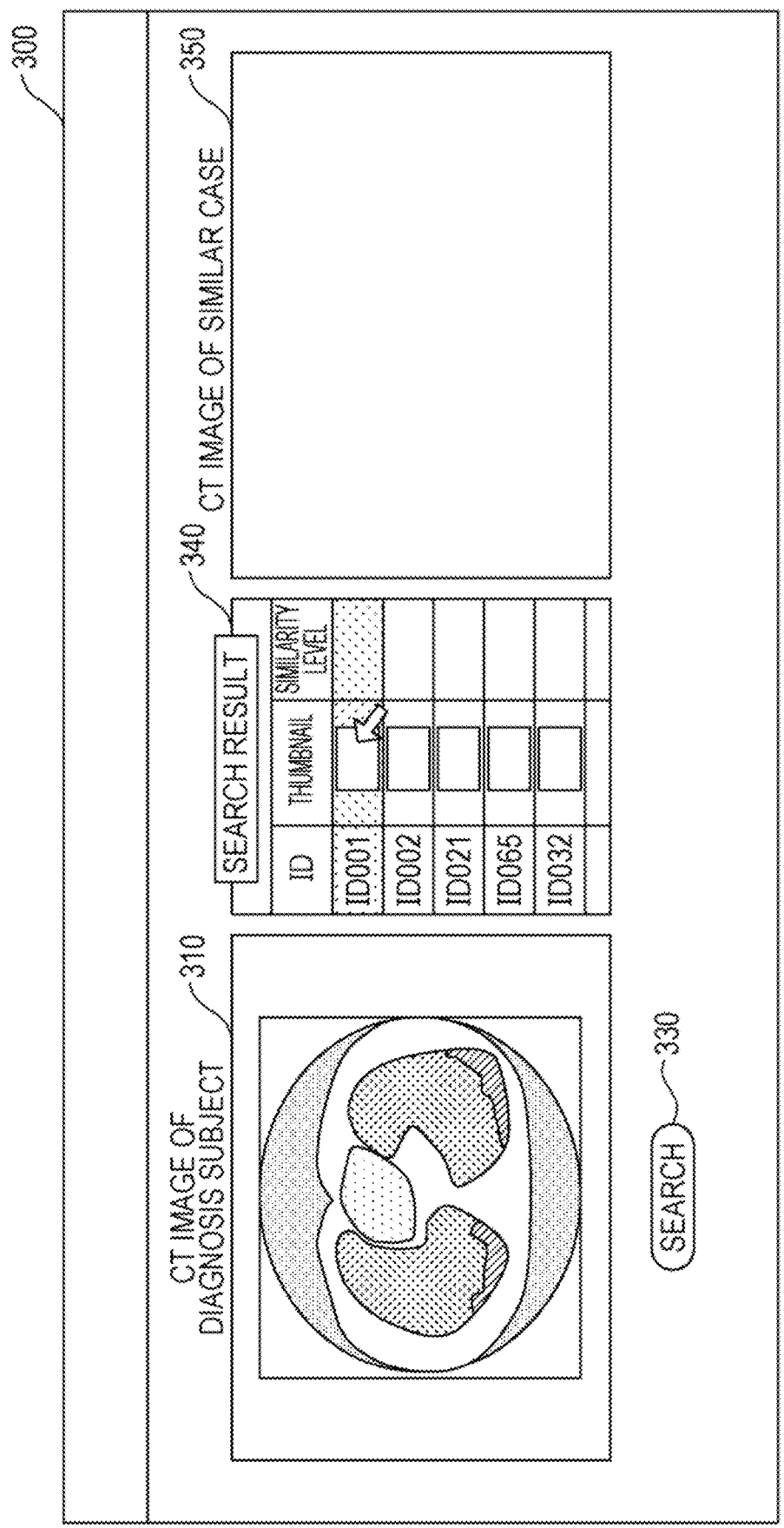

FIG. 5A

| ID | SLICE NUMBER | THUMBNAIL IMAGE | FEATURES INFORMATION | | | |
|---|---|---|---|---|---|---|
| | | | RIGHT LUNG FIELD | | LEFT LUNG FIELD | |
| | | | NUMBER OF LESION PIXELS IN PERIPHERAL AREA | NUMBER OF LESION PIXELS IN CENTRAL AREA | NUMBER OF LESION PIXELS IN PERIPHERAL AREA | NUMBER OF LESION PIXELS IN CENTRAL AREA |
| 100 | 001 | image101 | 23 | 245 | 372 | 34 |
| | 002 | image102 | 31 | 675 | 643 | 43 |
| | 003 | image103 | 29 | 547 | 621 | 36 |
| | ... | ... | ... | ... | ... | ... |

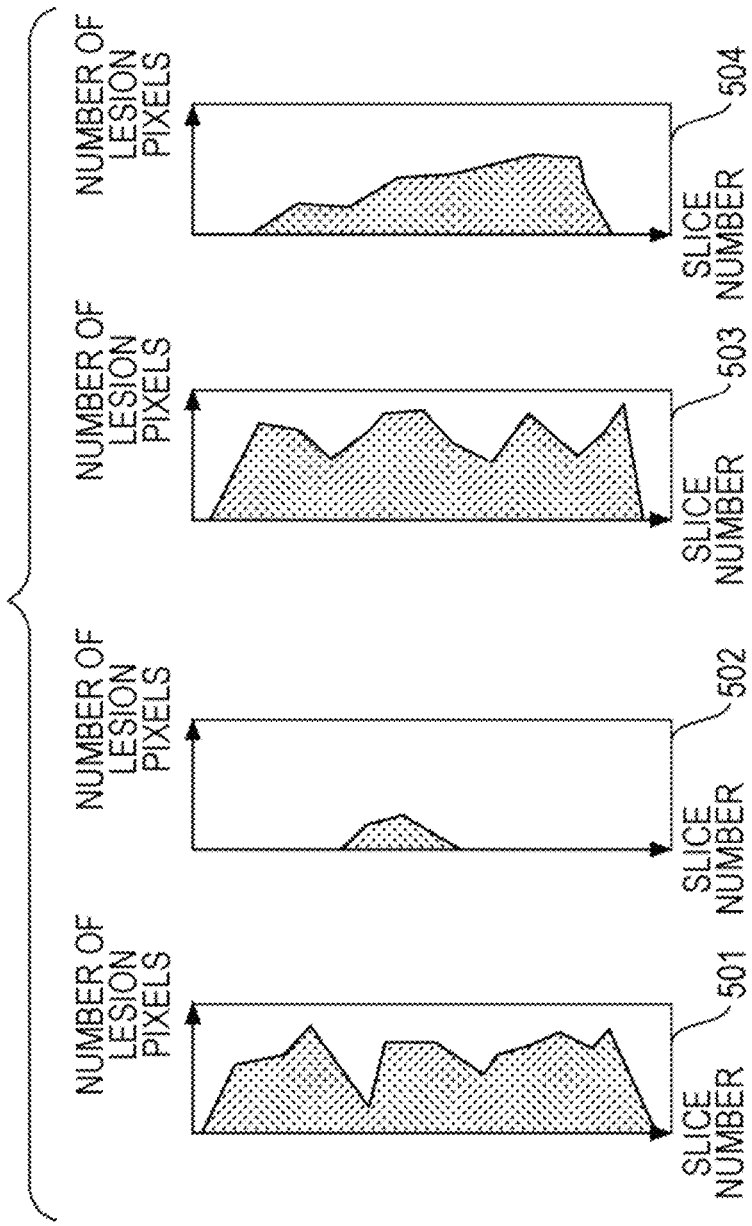

FIG. 6

| ID | IMAGE | CT IMAGE INFORMATION ||||||
| --- | --- | --- | --- | --- | --- | --- | --- |
| | | PATIENT INFORMATION |||| DIAGNOSIS RESULT | DIAGNOSTICIAN |
| | | PATIENT ID | NAME | AGE | SEX | | |
| 001 | IMAGE001 | | | | | | |
| 002 | IMAGE002 | | | | | | |
| 003 | IMAGE003 | | | | | | |
| 004 | IMAGE004 | | | | | | |

| ID | SLICE NUMBER | THUMBNAIL IMAGE | FEATURES INFORMATION ||||||
|---|---|---|---|---|---|---|---|---|
| | | | RIGHT LUNG FIELD ||| LEFT LUNG FIELD |||
| | | | NUMBER OF LESION PIXELS IN AREA 1 | ... | NUMBER OF LESION PIXELS IN AREA N | NUMBER OF LESION PIXELS IN AREA 1 | ... | NUMBER OF LESION PIXELS IN AREA N |
| 100 | 001 | image101 | 23 | ... | 245 | 372 | ... | 34 |
| | 002 | image102 | 31 | ... | 675 | 643 | ... | 43 |
| | 003 | image103 | ... | ... | ... | ... | ... | ... |
| | ... | ... | ... | ... | ... | ... | ... | ... |

1800

SIMILAR CASE IMAGE SEARCH PROGRAM, SIMILAR CASE IMAGE SEARCH APPARATUS, AND SIMILAR CASE IMAGE SEARCH METHOD

CROSS-REFERENCE TO RELATED APPLICATION

This application is a continuation application of International Application PCT/JP2018/002089 filed on Jan. 24, 2018 and designated the U.S., the entire contents of which are incorporated herein by reference. The International Application PCT/JP2018/002089 is based upon and claims the benefit of priority of the prior Japanese Patent Application No. 2017-046736, filed on Mar. 10, 2017, the entire contents of which are incorporated herein by reference.

FIELD

The embodiments discussed herein are related to a similar case image search program, a similar case image search apparatus, and a similar case image search method.

BACKGROUND

Conventionally, in health care sites, comparative interpretation of referring to previous cases similar to a case of a medical image of a diagnosis subject (similar case) to achieve diagnosis has been performed, and a similar case image search apparatus has been used as an apparatus for searching for the medical image of the similar case.

In the comparative interpretation, one of cases for radiologists and the like to be hard to diagnose images is diffuse lung disease. The diffuse lung disease is a disease, lesions of which are distributed over a wide range of a lung field area. In image diagnosis of diseases, lesions of which are distributed in organs, such as the diffuse lung disease, it is important to identify which site of the lung field area includes the lesions. For this reason, the similar case image search apparatus preferably divides the lung field area in the medical image of the diagnosis subject into areas suitable for the image diagnosis (for example, central area, peripheral area, and so on).

To address this, for example, Japanese Laid-open Patent Publication No. 2009-90054 proposes a division method of extracting the center of the patient's body from the medical image of the diagnosis subject, and dividing a particular area based on the distance from the extracted center.

However, the lung field area has a complicated shape, and is not symmetric about the center in the right-and-left direction as well as the fore-and-aft direction. For this reason, according to the division method, the lung field area may not be divided into areas suitable for the image diagnosis, and in an effort to determine the area where the lesions are distributed and to search for the similar case, it is difficult to accurately search for the similar case.

From an aspect, an object of the present disclosure is to search for the similar case based on the distribution of lesions in diseases, lesions of which are distributed in organs, such as the diffuse lung disease.

SUMMARY

According to an aspect of the embodiments, a similar case image search method includes: extracting a lung field area from a medical image and identifying a contour of the lung field area including a chest wall and a mediastinum; identifying a position at which the chest wall and the mediastinum are internally divided and dividing the lung field area into a central area and a peripheral area based on a shape of the lung field area; counting the number of pixels indicating lesions in each of the divided central area and peripheral area; and identifying a similar case image corresponding to similarity level of the number of pixels indicating lesions by referring to a storage unit that stores the number of pixels indicating lesions in each of the areas.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIGS. 4A and 4B are second views Illustrating an example of the display screen of the similar case image search apparatus;

FIGS. 5A and 5B are first views illustrating an example of features information stored in a features information DB;

FIG. 6 is a view illustrating an example of CT image information stored in an image DB;

FIG. 18 is a second view illustrating an example of the features Information stored in the features information DB.

DESCRIPTION OF EMBODIMENTS

Figure 1:
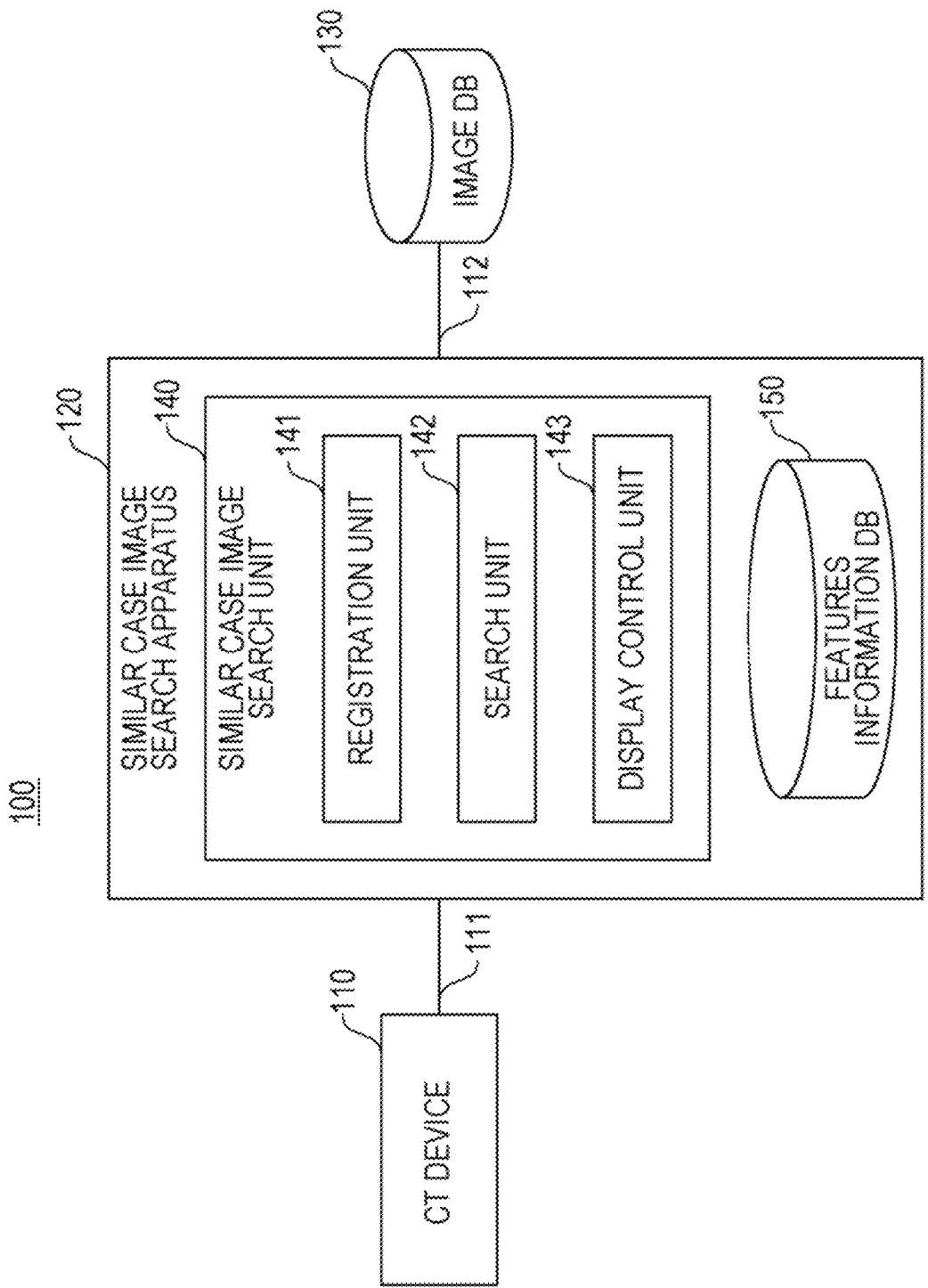
FIG. 1 is a view illustrating an example of a CT image processing system.

Embodiments will be described below with reference to appended figures. In this specification and the figures, constituents having the substantially same functions are given the same reference numerals, and redundant description thereof is omitted.

First Embodiment

<System Structure of CT Image Processing System>

First, a CT image processing system including a similar case image search apparatus in accordance with a first embodiment will be described. FIG. 1 is a view illustrating an example of the CT image processing system.

A CT image processing system 100 has a computed tomography (CT) device 110, a similar case image search apparatus 120, and an image database (database will be hereinafter abbreviated as DB) 130. The CT device 110 and the similar case image search apparatus 120 are connected to each other via wiring 111, and exchange various data. The similar case image search apparatus 120 and the image DB 130 are connected to each other via wiring 112, and exchange various data.

The CT device 110 scans the inside of the patient's body by radiation or the like, and executes processing by use of a computer to generate a CT image including a plurality of slice images of the patient, as a medical image (such processing will be hereinafter referred to as "capture the CT image"). The CT device 110 transmits the captured CT image to the similar case image search apparatus 120.

The similar case image search apparatus 120 installs a similar case image search program therein, and the similar case image search program is executed by the computer, causing the similar case image search apparatus 120 to function as a similar case image search unit 140.

The similar case image search unit 140 has a registration unit 141, a search unit 142, and a display control unit 143. The registration unit 141 stores the CT image captured by the CT device 110 in the image DB 130. For each of the slice images of the CT image, the registration unit 141 counts the number of pixels representing lesions (the number of lesion pixels) in each of lung fields, generating a histogram, and stores the histogram in a features Information DB 150.

For each of the slice images of the CT image of a diagnosis subject captured by the CT device 110, the search unit 142 counts the number of lesion pixels in each of the lung fields to generate histograms. The search unit 142 searches for a histogram that is similar to the histogram generated for the CT image of the diagnosis subject among histograms for CT images of search subjects, which are stored in the features information DB 150. In this manner, the search unit 142 searches for the CT image of a similar case similar to the CT image of the diagnosis subject. The search unit 142 notifies a search result to the display control unit 143.

The display control unit 143 displays a display screen for a radiologist or the like to compare and interpret the CT image of the diagnosis subject. The display screen includes a display function of displaying the CT image of the diagnosis subject. The display screen also includes an instruction function of searching for the CT image of the similar case similar to the case of the CT image of the diagnosis subject of the radiologist or the like. The display screen also includes a comparison display function of comparing the CT image read from the image DB 130 based on the search results of the search unit 142, as the CT image of the similar case, with the CT image of the diagnosis subject.

The image DB 130 stores the CT image captured by the CT device 110. In response to an instruction from the similar case image search apparatus 120, the image DB 130 transmits the stored CT image to the similar case image search apparatus 120.

<Hardware Configuration of Similar Case Image Search Apparatus>

Figure 2:
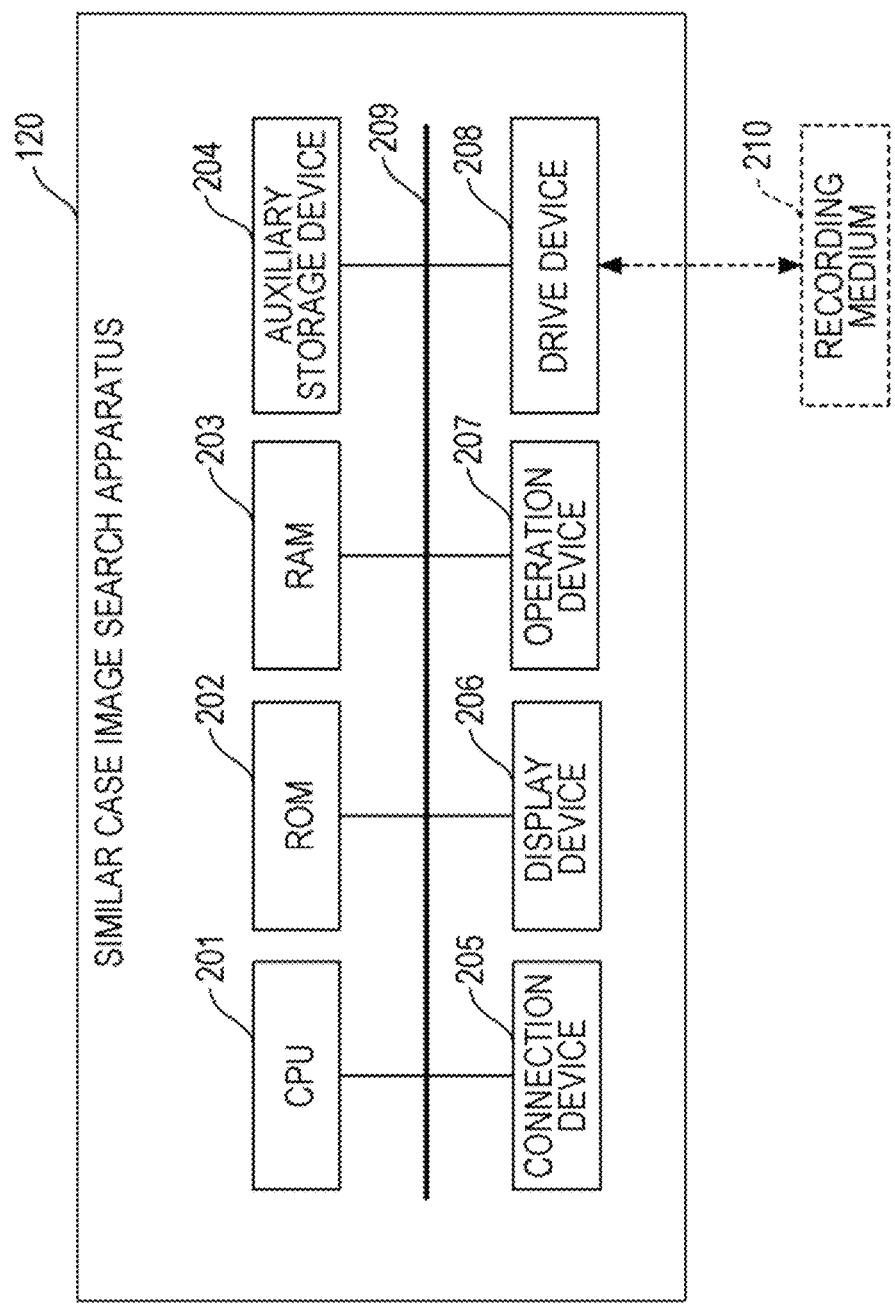
FIG. 2 is a view illustrating the hardware configuration of a similar case image search apparatus.

Next, the hardware configuration of the similar case image search apparatus 120 will be described. FIG. 2 is a view illustrating the hardware configuration of the similar case image search apparatus. As illustrated in FIG. 2, the similar case image search apparatus 120 includes a central processing unit (CPU) 201, a read only memory (ROM) 202, and a random access memory (RAM) 203. The CPU 201, the ROM 202, and the RAM 203 constitute a so-called computer.

The similar case image search apparatus 120 includes an auxiliary storage device 204, a connection device 205, a display device 206, an operation device 207, and a drive device 208. The hardware constituents of the similar case image search apparatus 120 are interconnected via a bus 209.

The CPU 201 executes various programs (for example, the similar case image search program) stored in the auxiliary storage device 204.

The ROM 202 is a nonvolatile memory. The ROM 202 functions as a main storage unit, which stores various programs and data for the CPU 201 to execute the various programs stored in the auxiliary storage device 204. Specifically, the ROM 202 stores boot programs including a basic input/output system (BIOS) and an extensible firmware interface (ER).

The RAM 203 is a volatile memory, and includes a dynamic random access memory (DRAM) and a static random access memory (SRAM). The RAM 203 functions as a main storage unit, which provides a work area expanded when the CPU 201 executes the various programs stored in the auxiliary storage device 204.

The auxiliary storage device 204 functions as a computer-readable auxiliary storage unit, which stores the various programs installed to the similar case image search apparatus 120, and data generated by executing the various programs. The features information DB 150 is implemented in the auxiliary storage device 204.

The connection device 205 is connected to the CT device 110 and the image DB 130, and transmits and receives various data to and from the CT device 110 and the image DB 130. Under the control of the display control unit 143, the display device 206 displays the display screen used when the radiologist or the like compares and interprets the CT image of the diagnosis subject. The operation device 207 accepts various operations of the radiologist or the like with respect to the similar case image search apparatus 120.

The drive device 208 is a device for setting a recording medium 210. The recording medium 210 described herein includes media that record data optically, electrically, or magnetically, for example, CD-ROMs, flexible discs, and magneto-optical discs. Alternatively, the recording medium 210 may include semiconductor memories that electrically record data, for example, ROMs and flash memories.

The various programs stored in the auxiliary storage device 204 are installed, for example, by setting the distributed recording medium 210 to the drive device 208 and reading various programs stored in the recording medium 210 using the drive device 208. Alternatively, the various programs stored in the auxiliary storage device 204 may be installed by downloading from a network via the connection device 205.

<Display Example of Display Screen>

Next, the display screen displayed on the display device 206 will be described. FIG. 3A to FIG. 4B are first views and second views illustrating an example of the display screen of the similar case image search apparatus, respectively.

Figure 3A:
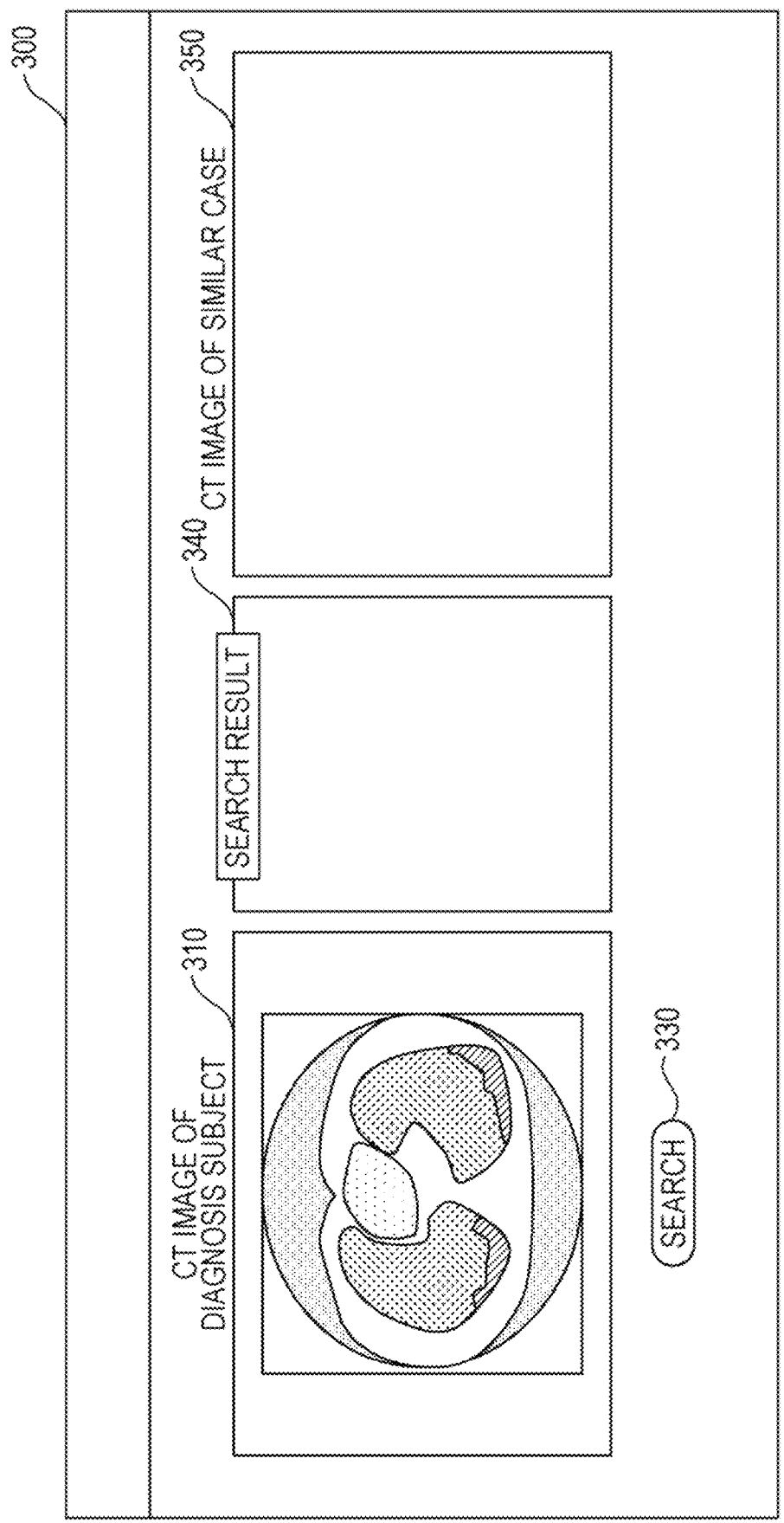
FIGS. 3A and 3B are first views illustrating an example of a display screen of the similar case image search apparatus.
Figure 3B:
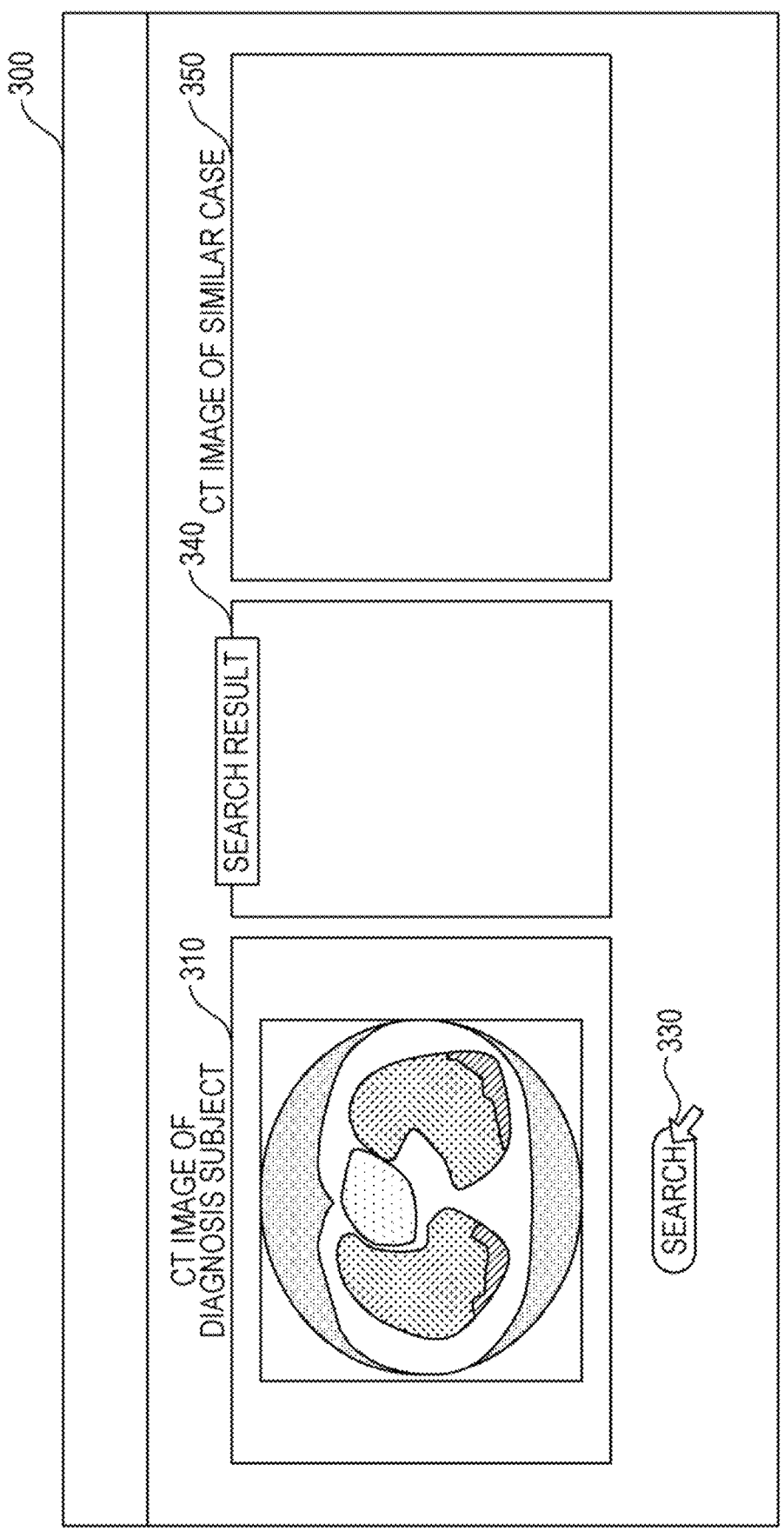

As illustrated in FIGS. 3A and 3B, a display screen 300 includes a diagnosis subject image display area 310, which displays a CT image of the diagnosis subject, which is captured by the CT device 110.

The display screen 300 includes a search button 330. The search button 330 is a button for instructing the search unit 142 to perform a search.

The display screen 300 includes a search result display area 340. The search result display area 340 displays search results acquired by causing the search unit 142 to search for the histogram similar to the histogram generated for the CT image of the diagnosis subject, among the histograms stored in the features information DB 150 for the CT images of the search subjects.

The display screen 300 includes a similar case search result display area 350. The similar case search result display area 350 displays a CT image designated by the radiologist or the like in the search results displayed in the search result display area 340.

FIG. 3A illustrates the case where the CT image of the diagnosis subject, which is captured by the CT device 110, is displayed in the diagnosis subject image display area 310 of the display screen 300.

FIG. 3B illustrates the case where the radiologist or the like presses the search button 330 in the state in which the CT image of the diagnosis subject is displayed in the diagnosis subject image display area 310 of the display screen 300. When the search button 330 is pressed, the display screen shifts to the display screen 300 illustrated in FIGS. 4A and 4B.

Figure 4A:
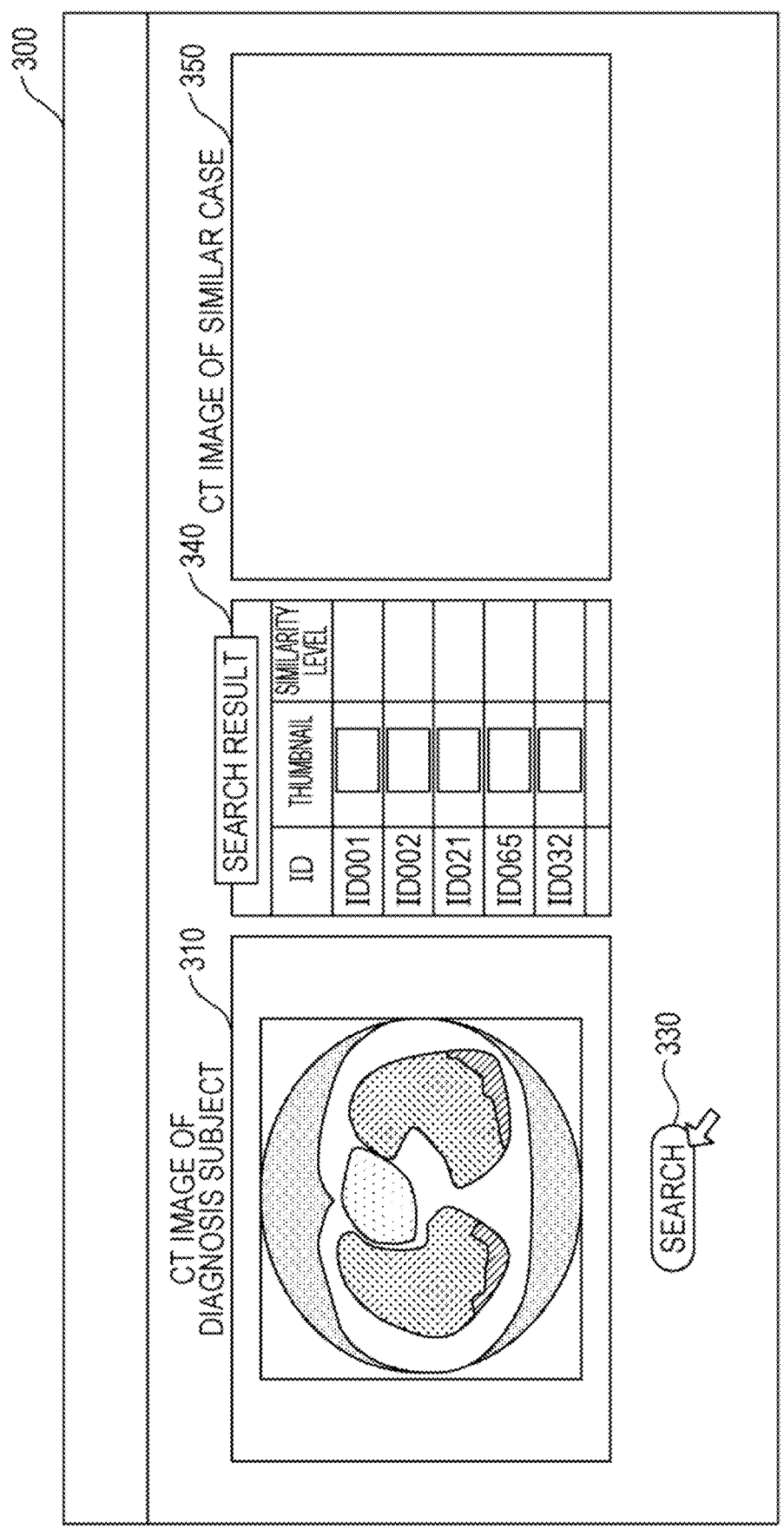

FIG. 4A illustrates the case where the search button 330 is pressed, causing the search unit 142 performs search and search results are displayed in the search result display area 340.

As illustrated in FIG. 4A, information items in the search results displayed in the search result display area 340 include "ID", "thumbnail", and "similarity level". The "ID" stores identifiers for identifying CT images searched by the search unit 142. The "thumbnail" displays thumbnail images of the CT Images Identified based on the "ID". The "similarity level" stores the similarity level between the histogram for each CT image searched by the search unit 142 and the histogram for the CT Image of the diagnosis subject.

FIG. 48 illustrates the case where a prescribed search result is selected from the search results displayed in the search result display area 340 by the radiologist or the like, and the CT image corresponding to the selected search result is displayed in the similar case search result display area 350.

Specifically, in the example illustrated in FIG. 4B, ID="ID001" is selected, and the corresponding CT image is displayed as the CT image of the similar case in the similar case search result display area 350. Thereby, the radiologist or the like may diagnose the CT image of the diagnosis subject by comparative interpretation while referring to the CT image of the similar case similar to the CT image of the diagnosis subject.

Display contents of display screen 300 are not limited to those illustrated in FIGS. 3A to 4B, and may display patient information of the patient to be diagnosed. Alternatively, the display screen may display various information that is associated with the CT image displayed on the similar case search result display area 350 and stored in the image DB 130.

<Features Information DB and Image DB>

Next, details of features information stored in the features information DB 150 and CT image information stored in the image DB 130 will be described.

(1) Details of Features Information

FIGS. 5A and 5B are first views illustrating an example of the features information stored in the features information DB. As illustrated in FIG. 5A, features information 500 includes "ID", "slice number", "thumbnail image", "right lung field", and "left lung field" as information items.

The "ID" stores identifiers for identifying CT images stored in the image DB 130. The "slice number" stores numbers for identifying a plurality of slice images included in each CT image. The "thumbnail image" stores thumbnail images of the plurality of slice images included in the CT image, which are associated with the respective slice number.

The "right lung field" further includes "number of lesion pixels in peripheral area" and "number of lesion pixels in central area". The "number of lesion pixels in peripheral area" stores the number of lesion pixels of lesions distributed in a peripheral area of the right lung field. The "number of lesion pixels in central area" stores the number of lesion pixels of lesions distributed in a central area of the right lung field.

Similarly, the "left lung field" further includes "number of lesion pixels in peripheral area" and "number of lesion pixels in central area". The "number of lesion pixels in peripheral area" stores the number of lesion pixels of lesions distributed in a peripheral area of the left lung field. The "number of lesion pixels in central area" stores the number of lesion pixels of lesions distributed in a central area of the left lung field.

FIG. 5B illustrates histograms of the number of lesion pixels generated based on the features information 500, a horizontal axis represents the number of lesion pixels, and a vertical axis represents the slice number. Among the histograms, a histogram 501 is a histogram of the number of lesion pixels in peripheral area of the right lung field, and a histogram 502 is a histogram of the number of lesion pixels in central area of the right lung field. A histogram 503 is a histogram of the number of lesion pixels in peripheral area of the left lung field, and a histogram 504 is a histogram of the number of lesion pixels in central area of the left lung field. The histograms 501 to 504 are associated with the "ID" in the features information 500, and stored in the features information DB 150.

(2) Details of CT Image Information

FIG. 6 is a view illustrating the CT image information stored in the image DB. As Illustrated in FIG. 6, a CT image Information 600 includes "ID", "image", "patient Information", "diagnosis result", "diagnostician" as information items.

The "ID" stores identifiers for identifying CT images stores in the image DB 130. The "image" includes file names of the CT images stored in the image DB 130. The "patient information" stores detailed information (patient ID, name, age, and sex) of the patient whose CT image is captured. The "diagnosis result" stores diagnosis results of the CT images, which are acquired by the radiologists or the like. The "diagnostician" stores IDs of the radiologists or the like who diagnose respective CT images. In the first embodiment, the diagnosis of the CT image stored in the image DB 130 may be made at taking of the CT image.

The CT image information 600 may store, in addition to the diagnosis result, various information including contents of a procedure for the patient, and the state after the procedure, which is associated with the diagnosis result.

<Details of Each Unit of Similar Case Image Search Apparatus and Specific Examples of Processing of Each Unit>

Next, among the units (the registration unit 141, the search unit 142, and the display control unit 143) of the similar case image search apparatus 120, details of the registration unit 141 and the search unit 142, and specific examples of the processing of the registration unit 141 and the search unit 142 will be sequentially described.

(1) Details of Registration Unit

Figure 7:
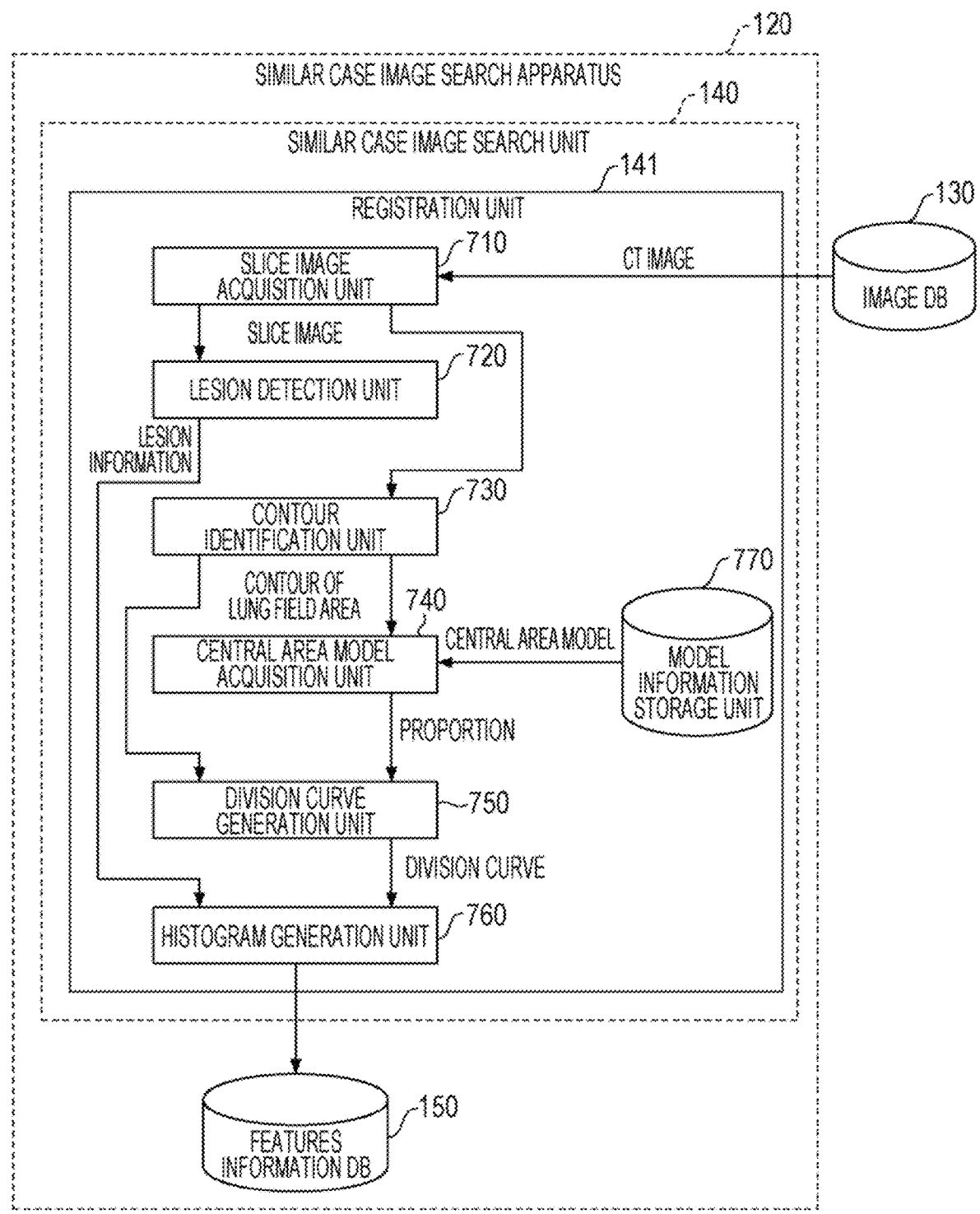
FIG. 7 is a first view illustrating an example of the functional configuration of a registration unit of the similar case image search apparatus.

First, details of the registration unit 141 will be described. FIG. 7 is a first view Illustrating an example of the functional configuration of the registration unit of the similar case image search apparatus. As illustrated in FIG. 7, the registration unit 141 has a slice image acquisition unit 710, a lesion detection unit 720, a contour identification unit 730, a central area model acquisition unit 740, a division curve generation unit 750, and a histogram generation unit 760.

When the radiologist or the like inputs the patient information and then, captures a CT image of the patient in the CT device 110 and Inputs diagnosis result of the captured CT image, the captured CT image is stored in the image DB 130. The CT image information 600 stores the ID for identifying the stored CT image, the file name, the patient Information, the diagnosis result, and the ID for identifying the radiologist who diagnoses the CT image, which are associated with the CT image.

When a new CT image is stored in the image DB 130, and the ID for identifying the stored CT image, the file name, the patient information, the diagnosis result, and the ID for identifying the radiologist who diagnoses the CT image are stored in the CT image information 600, each unit of the registration unit 141 in FIG. 7 are activated.

The slice image acquisition unit 710 reads each of slice images included of the CT image newly stored in the image DB 130, and transmits the slice image to the lesion detection unit 720 and the contour identification unit 730.

The lesion detection unit 720 executes lesion detection processing. Specifically, the lesion detection unit 720 divides each slice image into grids each having a designated size to generate partial images (hereinafter referred to as "block"). The lesion detection unit 720 statistically processes the brightness value of each pixel of each of the generated blocks, thereby calculating a multidimensional vector. Further, based on the calculated multidimensional vector, the lesion detection unit 720 determines whether or not each block corresponds to a lesion.

In determining whether or not each block corresponds to the lesion based on the calculated multidimensional vector, it is assumed that the lesion detection unit 720 previously holds a representative vector indicating the lesion. The lesion detection unit 720 calculates a distance between the multidimensional vector calculated from each block and the previously-held representative vector indicating the lesion, thereby determining whether or not each block corresponds to the lesion to detect the lesion.

The lesion detection unit 720 notifies lesion Information Indicating the position of the detected lesion to the histogram generation unit 760.

The contour identification unit 730 executes contour identification processing for each slice image. Specifically, the contour identification unit 730 extracts the lung field area from each slice image, and identifies the contour of the extracted lung field area. The contour identification unit 730 notifies the identified contour of the lung field area of each slice image to the central area model acquisition unit 740 and the division curve generation unit 750.

The central area model acquisition unit 740 executes central area model acquisition processing. Specifically, the central area model acquisition unit 740 reads a central area model previously stored in a model information storage unit 770. The central area model is a model defining the proportion of the central area and the peripheral area in the lung field area at each slice position.

The central area model acquisition unit 740 acquires the central area model to identify the proportion of the central area and the peripheral area in the lung field area of each slice image, and notifies the proportion to the division curve generation unit 750.

The division curve generation unit 750 is an example of the division unit, and executes division curve generation processing. Specifically, the division curve generation unit 750 internally divides the contour of the lung field area of each slice image, which is notified from the contour identification unit 730, based on the proportion notified from the central area model acquisition unit 740 for each slice image, thereby calculating division points. The division curve generation unit 750 connects the calculated division points to each other to generate a division curve dividing the lung field area into the central area and the peripheral area. Further, the division curve generation unit 750 notifies the division curve generated for each slice image to the histogram generation unit 760.

The histogram generation unit 760 is an example of a counting unit, and compares the lesion information about each slice image, which is notified from the lesion detection unit 720, with the division curve in each slice image, which is notified from the division curve generation unit 750. Thereby, the histogram generation unit 760 may determine whether each lesion in each slice image is distributed in the central area or the peripheral area.

For each slice image in the right lung field and the left lung field, the histogram generation unit 760 counts the number of lesion pixels of lesions distributed in the central area and the number of lesion pixels of lesions distributed in the peripheral area. The histogram generation unit 760 stores the counted number of lesion pixels in the features information DB 150.

Further, the histogram generation unit 760 generates a histogram based on the counted number of lesion pixels, and stores the histogram in association with "ID" in the features information 500.

(2) Specific Examples of Processing of Registration Unit

Next, specific examples of the registration unit 141 of the similar case image search apparatus 120 will be described.

(i) Specific Example of Lesion Detection Processing of Lesion Detection Unit

Figure 8A:
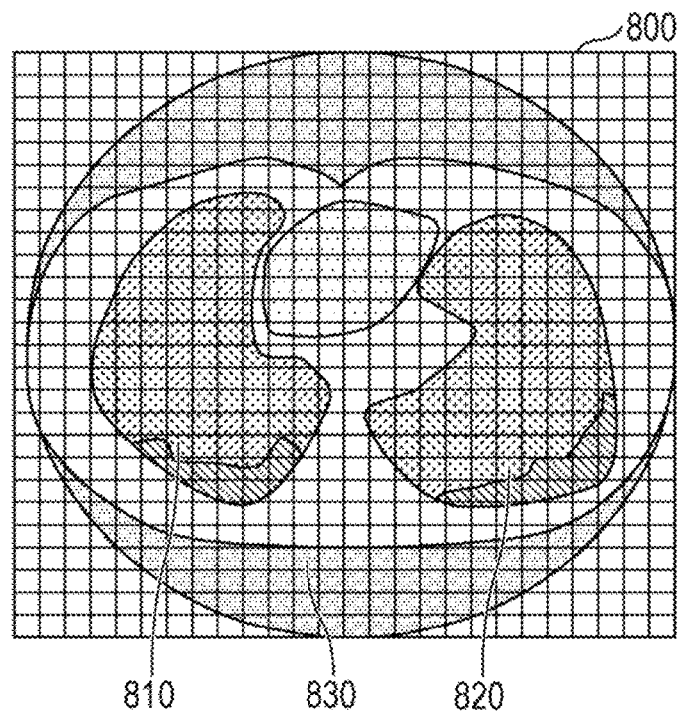
FIGS. 8A and 8B are views illustrating a specific example of lesion detection processing of a lesion detection unit.
Figure 8B:
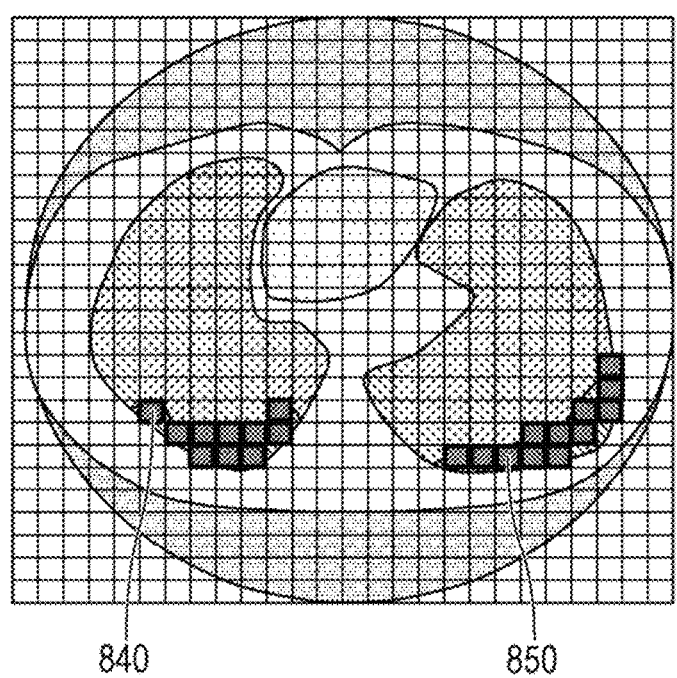

First, a specific example of the lesion detection processing of the lesion detection unit 720 of the registration unit 141 will be described. FIGS. 8A and 8B are views illustrating the specific example of the lesion detection processing of the lesion detection unit.

FIG. 8A illustrates an example of the slice image. As Illustrated in FIG. 8A, a slice image 800 includes a lung field area 810 of a right lung of a patient, and a lung field area 820 of a left lung of the patient. The blocks (for example, block 830) in the slice image 800 are blocks generated by the lesion detection unit 720.

FIG. 8B illustrates the case of determining whether or not each block generated by the lesion detection unit 720 corresponds to the lesion. Among the blocks illustrated in FIG. 8B, blocks represented by thick lines (for example, blocks 840 and 850) are blocks determined as lesions. On the contrary, blocks other than the blocks represented by the thick lines (for example, blocks 840 and 850) are blocks determined as non-lesions.

Figure 9A:
FIGS. 9A and 9B are views illustrating an example of contour identification processing of a contour identification unit.
Figure 9B:
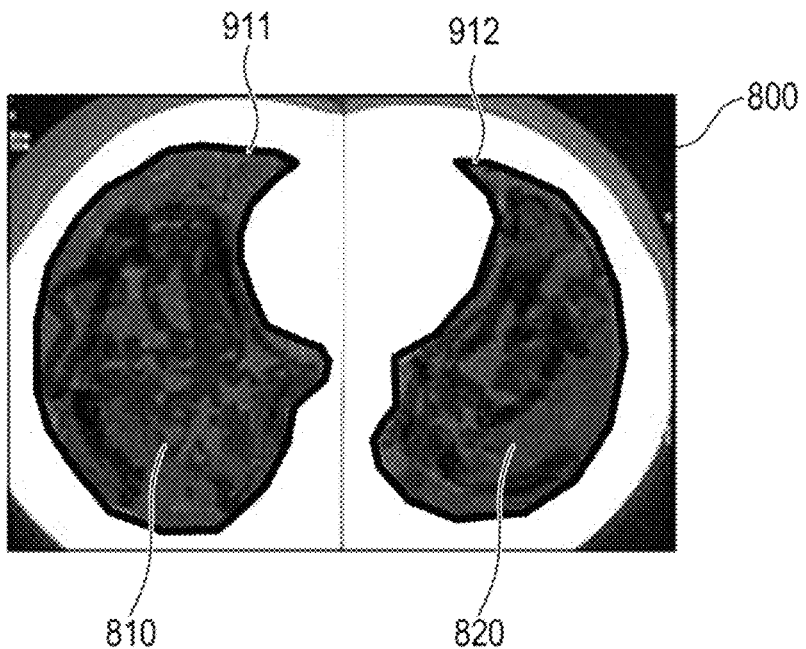

(ii) Specific Example of Contour Identification Processing of Contour Identification Unit Subsequently, a specific example of contour identification processing of the contour identification unit 730 will be described. FIGS. 9A and 9B are views illustrating the specific example of the contour identification processing of the contour identification unit. FIG. 9A illustrates the slice image 800 acquired before the contour identification processing of the contour identification unit 730. FIG. 9B illustrates the case where the contour identification unit 730 extracts the lung field areas 810, 820 from the slice image 800, and identifies contours 911, 912 of the lung field areas 810, 820.

(iii) Specific Example of Central Area Model Acquisition Processing of Central Area Model Acquisition Unit Subsequently, a specific example of central area model acquisition processing of the central area model acquisition unit 740 will be described. Usually, lung tissues three-dimensionally spread from a site called the hilum of lung, and following medical findings about the central area in each slice position are obtained.

In the slice position including the hilum of lung, the area of the central area becomes maximum.

As the slice position is away from the slice position including the hilum of lung, the area of the central area becomes smaller and finally, becomes 0.

There is a certain gap between the upper end of the lung field area to the upper end of the central area. There is a certain gap between the lower end of the lung field area and the lower end of the central area.

Figure 10:
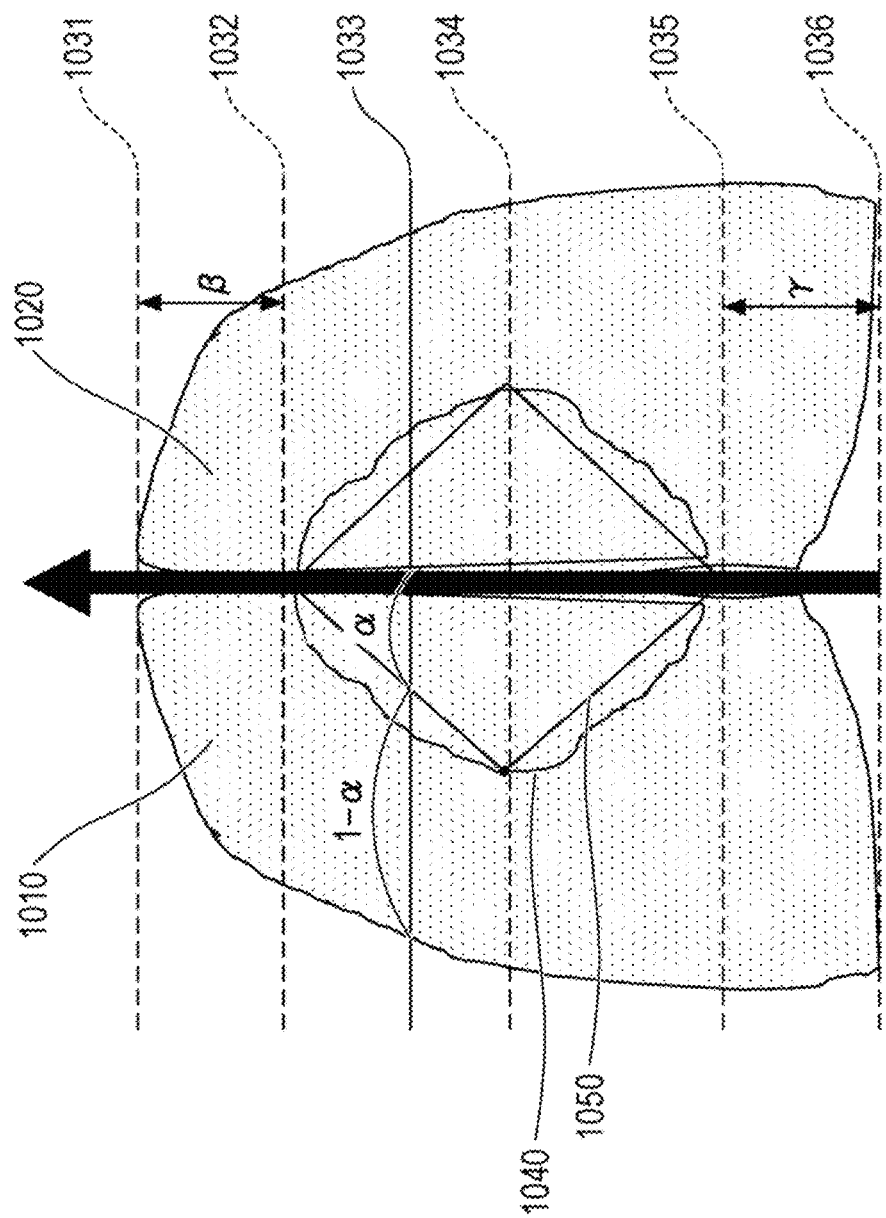
FIG. 10 is a view illustrating an example of a central area model.

The central area model acquired by the central area model acquisition unit 740 is generated based on the above-mentioned medical findings. FIG. 10 is a view Illustrating an example of the central area model, and illustrates the case where a central area model 1050 is superimposed on the lung field areas 1010, 1020 when viewing the patient's lung from the front.

In the central area model 1050, a slice position 1034 passes the hilum of lung, the area of the central area becomes maximum at the slice position 1034. A slice position 1031 passes the upper ends of the lung field areas 1010, 1020, and a slice position 1032 passes the upper end of a central area 1040. A gap β is present between the slice position 1031 and the slice position 1032. A slice position 1036 passes the lower ends of the lung field areas 1010, 1020, and a slice position 1035 passes the lower end of the central area 1040. A gap γ is present between the slice position 1036 and the slice position 1035.

The central area model 1050 is linearly approximated such that the area of the central area becomes maximum at the slice position 1034, and becomes 0 at the slice position 1032 and the slice position 1035.

The central area model 1050 defines, at each slice position, a proportion of a length from the center to a boundary of the central area model 1050 and a length from the boundary of the central area model 1050 to each of boundaries of the lung field areas 1010, 1020. In the example illustrated in FIG. 10, the central area model 1050 defines, at a slice position 1033, the proportion of the length from the center to the boundary of the central area model 1050 and the length from the boundary of the central area model 1050 to the boundary of the lung field area 1010 as $\alpha:(1-\alpha)$.

The central area model acquisition unit 740 executes the central area model acquisition processing to acquire the central area model 1050. Based on the central area model 1050, the central area model acquisition unit 740 determines the proportion of the length from the center of each slice position to the boundary of the central area model 1050 and the length from the boundary of the central area model 1050 to the boundary of each of the lung field areas 1010, 1020.

Figure 11:
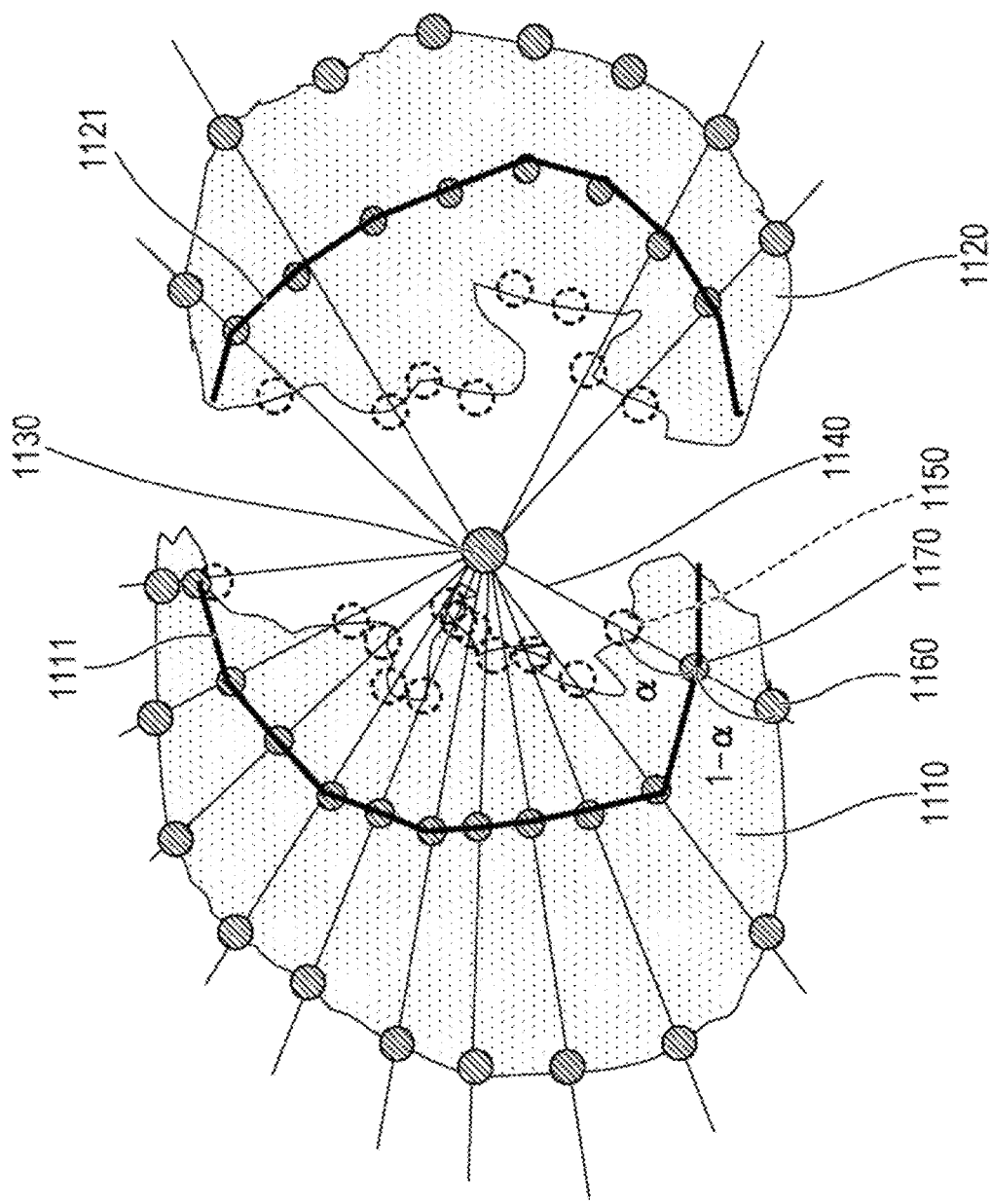
FIG. 11 is a view illustrating a specific example of division curve generation processing of a division curve generation unit.

(iv) Specific Example of Division Curve Generation Processing of Division Curve Generation Unit Subsequently, a specific example of division curve generation processing of the division curve generation unit 750 will be described. FIG. 11 is a view illustrating the specific example of the division curve generation processing of the division curve generation unit. FIG. 11 illustrates the case where division curves 1111, 1121 dividing the lung field area into the central area and the peripheral area are generated in the slice image at the slice position 1033.

The division curve generation unit 750 extracts a central position 1130 of the patient's body from the slice image. The division curve generation unit 750 radially extends straight lines from the central position 1130, and extracts intersections between the straight lines and the contours of the lung field areas 1110, 1120, which are notified from the contour identification unit 730 (inner (mediastinum) intersections and outer (chest wall) intersections).

For example, the division curve generation unit 750 extends a straight line 1140 from the central position 1130, and extracts intersections between the straight line and the contour of the lung field area 1110 (an inner (mediastinum) Intersection 1150 and an outer (chest wall) intersection 1160).

Subsequently, the division curve generation unit 750 internally divides line segments between the inner (mediastinum) intersections and the outer (chest wall) intersections based on the proportion notified from the central area model acquisition unit 740, to identify the division points.

For example, the division curve generation unit 750 internally divides the line segment between the inner (mediastinum) intersection 1150 and the outer (chest wall) intersection 1160 based on the proportion $\alpha:(1-\alpha)$ to identify a division point 1170.

The division curve generation unit 750 identifies each straight line radially extending from the central position 1130 to identify the division point, and connects the identified division points to each other, thereby generating division curves based on the shape of the lung field areas 1110, 1120. Thereby, the division curve generation unit 750 may generate the division curve 1111 for the lung field area 1110 and the division curve 1121 for the lung field area 1120. That is, the lung field areas 1110, 1120 each may be divided into the central area and the peripheral area based on medical findings.

(3) Details of Search Unit

Next, among the units (the registration unit 141, the search unit 142, and the display control unit 143) of the similar case image search apparatus 120, the search unit 142 will be described in detail.

Figure 12:
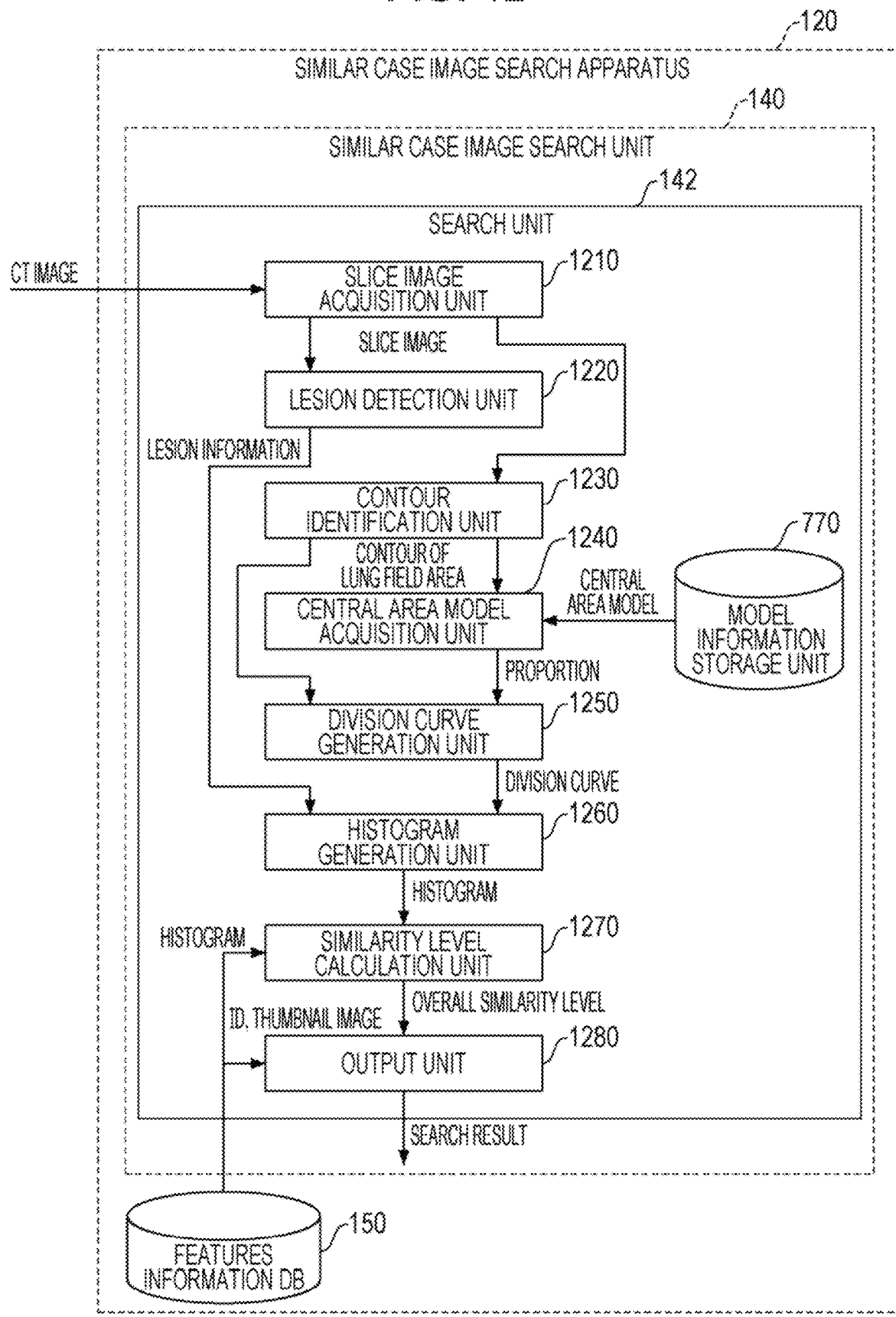
FIG. 12 is a view illustrating an example of the functional configuration of a search unit of the similar case image search apparatus.

FIG. 12 is a view illustrating an example of the functional configuration of the search unit of the similar case image search apparatus. As Illustrated in FIG. 12, the search unit 142 has a slice image acquisition unit 1210, a lesion detection unit 1220, a contour identification unit 1230, a central area model acquisition unit 1240, a division curve generation unit 1250, a histogram generation unit 1260, a similarity level calculation unit 1270, and an output unit 1280.

When the radiologist or the like activates the search unit 142 and Inputs patient information about the patient to be diagnosed and then, the CT device 110 captures a CT image of the patient, the display control unit 143 displays the captured CT image as the CT image of the diagnosis subject on the display screen 300. The display control unit 143 displays the display screen 300 and the radiologist or the like inputs a search instruction, activating each of the units of the search unit 142 in FIG. 12.

Among the units of the search unit 142, the units except for the similarity level calculation unit 1270 and the output unit 1280 execute processing for the CT image of the diagnosis subject on the display screen 300, as well as the same processing as the processing of the registration unit 141 in FIG. 7. Thus, description of the same processing is omitted.

The similarity level calculation unit 1270 is an example of the image identification unit. The similarity level calculation unit 1270 calculates the similarity level between histograms for the CT Image of the diagnosis subject and histograms for the CT image of the search subject, which is read from the features information DB 150. The similarity level calculation unit 1270 calculates the similarity level about each of the histograms of the central area and the peripheral area in the right lung field, and the similarity level about each of the histograms of the central area and the peripheral area in the left lung field. The similarity level calculation unit 1270 sums the calculated similarity level to calculate a total value (overall similarity level). The similarity level calculation unit 1270 notifies the overall similarity level calculated between the CT image of the diagnosis subject and the CT image of each search subject to the output unit 1280.

The output unit 1280 sorts the overall similarity level notified from the similarity level calculation unit 1270 and rearranges the overall similarity level in decreasing order. The output unit 1280 reads the IDs and the thumbnail Images that correspond to a predetermined number of search subjects having high overall similarity level from the features information DB 150, and notifies the IDs and the thumbnail images along with the overall similarity level as the search results to the display control unit 143.

(4) Specific Examples of Processing of Search Unit

Figure 13:
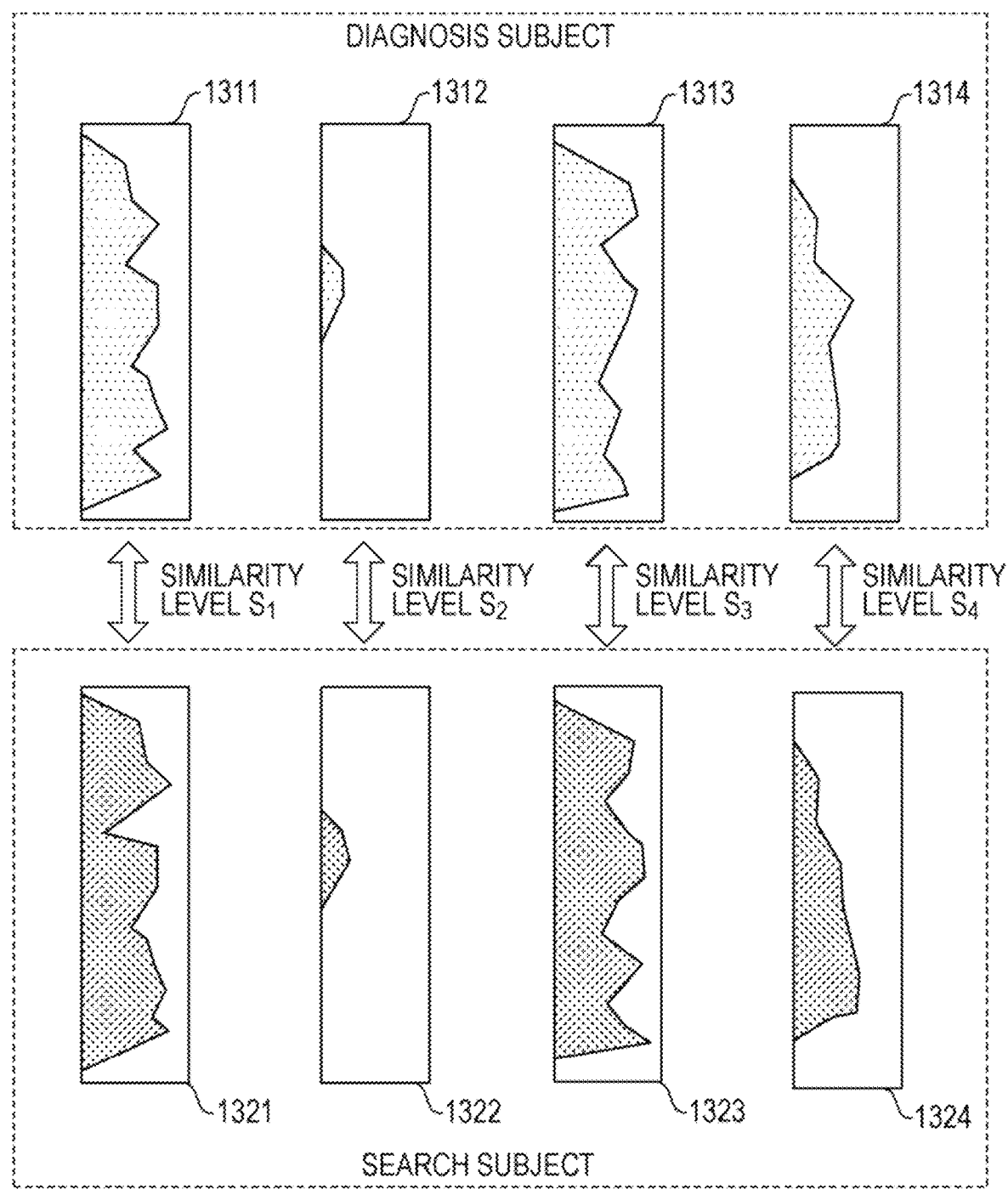
FIG. 13 is a view illustrating a specific example of similarity level calculation processing of a similarity level calculation unit.

Next, out of processing of the search unit 142 of the similar case image search apparatus 120, a specific example of similarity level calculation processing of the similarity level calculation unit 1270 will be described. FIG. 13 is a view Illustrating a specific example of the similarity level calculation processing of the similarity level calculation unit.

In FIG. 13, histograms 1311 to 1314 are histograms of the CT image of the diagnosis subject. Among the histograms, the histogram 1311 is the histogram for the peripheral area in the right lung field, and the histogram 1312 is the histogram for the central area in the right lung field. The histogram 1313 is the histogram for the peripheral area in the left lung field, and the histogram 1314 is the histogram for the central area in the left lung field.

Histograms 1321 to 1324 are histograms of the CT image of the diagnosis subject. Among the histograms, the histogram 1321 is the histogram for the peripheral area in the right lung field, and the histogram 1322 is the histogram for the central area in the right lung field. The histogram 1323 is the histogram for the peripheral area in the left lung field, and the histogram 1324 is the histogram for the central area in the left lung field.

The similarity level calculation unit 1270 calculates the similarity level of mutual histograms, and sums the similarity level to calculate the overall similarity level. In the example Illustrated in FIG. 13, the similarity level for the histograms for the peripheral area in the right lung field is $S_1$, and the similarity level for the histograms of the central area in the right lung field is $S_2$. In the example illustrated in FIG. 13, the similarity level for the histograms of the peripheral area in the left lung field is $S_3$, and the similarity level for the central area in the left lung field is $S_4$. Accordingly, the similarity level calculation unit 1270 calculates the overall similarity level between the CT image of the diagnosis subject and the CT image of the search subject as $S=S_1+S_2+S_3+S_4$.

<Entire Flow of Similar Case Image Search Processing in CT Image Processing System>

Figure 14:
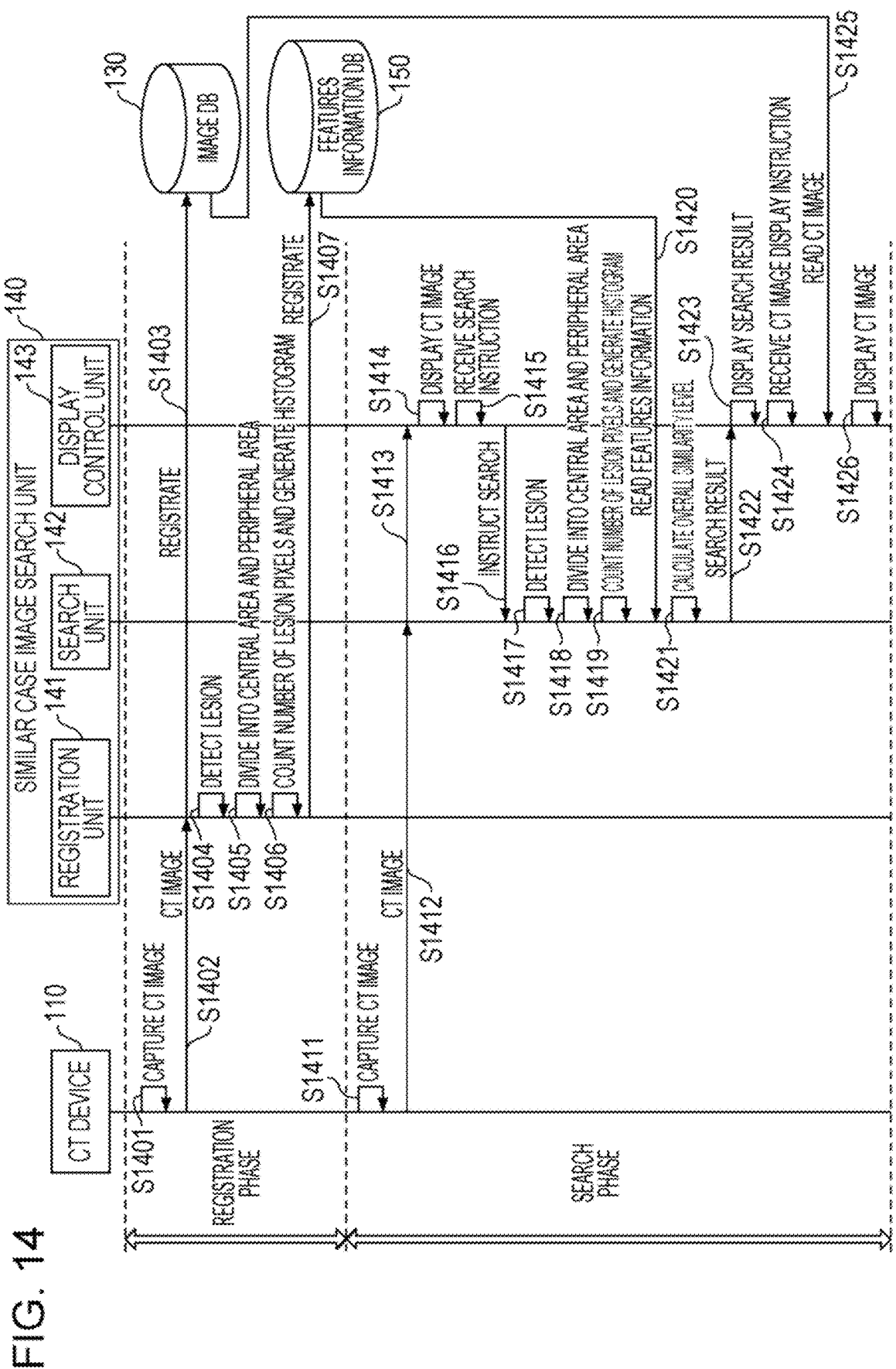
FIG. 14 is a sequence diagram illustrating similar case image search processing of a CT image processing system.

Next, the entire flow of similar case image search processing in the CT image processing system 100 will be described. FIG. 14 is a sequence diagram of the similar case image search processing in the CT image processing system.

As Illustrated in FIG. 14, the similar case image search processing in the CT image processing system 100 may be roughly divided into a registration phase and a search phase. First, registration phase will be described.

In Step S1401, the CT device 110 a patients CT image. At capturing of the CT image, patient information is inputted to the similar case Image search apparatus 120.

In Step S1402, the CT device 110 transmits the captured CT Image as the CT image of the search subject to the registration unit 141 of the similar case image search apparatus 120.

In Step S1403, the registration unit 141 receives the CT image of the search subject from the CT device 110, adds an identifier to the CT Image, and stores the CT image along the patient information in the image DB 130. When the registration unit 141 stores the CT image in the image DB 130, the radiologist or the like diagnoses the CT image. The registration unit 141 associates a diagnosis result with the CT image, and stores them in the image DB 130.

In Step S1404, the registration unit 141 applies the lesion detection processing to each slice image of the stored CT image of the search subject, and detects lesions.

In Step S1405, the registration unit 141 applies the contour identification processing, the central area model acquisition processing, and the division curve generation processing to each slice image of the stored CT image of the search subject, thereby dividing the lung field area into the central area and the peripheral area.

In Step S1406, the registration unit 141 counts the number of lesion pixels of lesions distributed in the central area and the number of lesion pixels of lesions distributed in the peripheral area to generate the histograms 1321 to 1324.

In Step S1407, the registration unit 141 stores the counted number of lesion pixels and the generated histograms in the features information 500 of the features information DB 150.

Thus, the registration phase is completed. FIG. 14 illustrates the example of the processing for one patient in the registration phase. In fact, however, a plurality of patients are subjected to the processing in the registration phase.

Subsequently, the search phase will be described. In Step S1411, the CT device 110 captures a CT Image of a patient to be diagnosed. At capturing of the CT image in Step S1411, patient information on the patient to be diagnosed is inputted to the similar case image search apparatus 120.

In Step S1412, the CT device 110 transmits the captured CT image as the CT image of the diagnosis subject to the search unit 142 of the similar case image search apparatus 120.

In Step S1413, the search unit 142 receives the CT image of the diagnosis subject from the CT device 110. The search unit 142 notifies the acquired CT image of the diagnosis subject to the display control unit 143.

In Step S1414, the display control unit 143 displays the display screen 300 on the display device 206, and displays any slice image inclined in the CT image notified from the search unit 142 on the diagnosis subject image display area 310 of the display screen 300.

In Step S1415, the display control unit 143 accepts a search instruction inputted via the search button 330 of the display screen 300.

In Step S1416, the display control unit 143 notifies the accepted search instruction to the search unit 142.

In Step S1417, when receiving the search Instruction from the display control unit 143, the search unit 142 executes the lesion detection processing for each slice image of the CT image of the diagnosis subject, and detects lesions.

In Step S1418, the search unit 142 executes the contour identification processing, the central area model acquisition processing, and the division curve generation processing for each slice image of the CT image of the diagnosis subject, thereby dividing the lung field area into the central area and the peripheral area.

In Step S1419, the search unit 142 counts the number of lesion pixels of lesions distributed in the central area and the number of lesion pixels of lesions distributed in the peripheral area, and generates the histograms 1311 to 1314.

In Step S1420, the search unit 142 reads the features information 500 from the features information DB 150, and acquires histograms (for example, histogram 1321 to 1324) of the CT image of each search subject.

In Step S1421, the search unit 142 calculates the similarity level for each area between the acquired histograms 1321 to 1324 for the CT image of the search subject and the generated histograms 1311 to 1314 for the CT image of the diagnosis subject, respectively. The search unit 142 sums the similarity level calculated for each area to calculate the overall similarity level, and sorts the calculated overall similarity level in descending order.

In Step S1422, the search unit 142 notifies the IDs and the thumbnail images which are associated with the CT Images of a predetermined number of search subjects having high overall similarity level, along with the overall similarity level, as the search results to the display control unit 143.

In Step S1423, the display control unit 143 displays the search result notified from the search unit 142 on the search result display area 340.

In Step S1424, when the radiologist or the like selects a prescribed search result in the search result display area 340, the display control unit 143 accepts it as an instruction to display the CT image.

In Step S1425, the display control unit 143 identifies the ID included in the selected search result, and reads the CT image determined based on the identified ID from the image DB 130.

In Step S1426, the display control unit 143 displays any slice image of the read CT image on the similar case search result display area 350. Thereby, the radiologist or the like may diagnose the CT image of the diagnosis subject by comparative interpretation while referring to the slice image of the CT image of the similar case similar to the case of the CT image of the diagnosis subject.

As apparent from the above description, in the case of diseases, lesions of which are distributed in organs, such as the diffuse lung disease, the lesions are distributed over a wide range of the lung field area. Conventionally, however, the lung field area may be properly divided into the central area and the peripheral area. For this reason, when it is attempted to determine the distributed area of lesions and search for a similar case, it is difficult to accurately search for the similar case.

On the contrary, the similar case image search apparatus 120 identifies the position at which the chest wall and the mediastinum are internally divided in each slice image, based on medical findings, to divide the lung field area into the central area and the peripheral area. For this reason, the similar case image search apparatus 120 may divide the lung field area into areas suitable for diagnosis.

For the lesions detected in each slice image, the similar case image search apparatus 120 counts the number of lesion pixels of lesions distributed in the central area and the number of lesion pixels of lesions distributed in the peripheral area, and generates histograms. Further, the similar case image search apparatus 120 calculates the similarity level using the generated histograms to identify the similar case image. Therefore, the similar case image search apparatus 120 may determine the distributed area of lesions to search for the similar case.

As a result, the similar case image search apparatus 120 may accurately search for the similar case based on the distribution of lesions in diseases, lesions of which are distributed in organs, such as the diffuse lung disease.

Second Embodiment

In the first embodiment, for each slice image, the division curve is generated to divide the lung field area into the central area and the peripheral area. However, the method of dividing the lung field area into the central area and the peripheral area is not limited to this. In a second embodiment, the lung field area is divided into the central area and the peripheral area by a method that is different from the method in the first embodiment. A difference between this embodiment and the first embodiment will be mainly described below.

<Functional Configuration of Registration Unit of Similar Case Image Search Apparatus>

Figure 15:
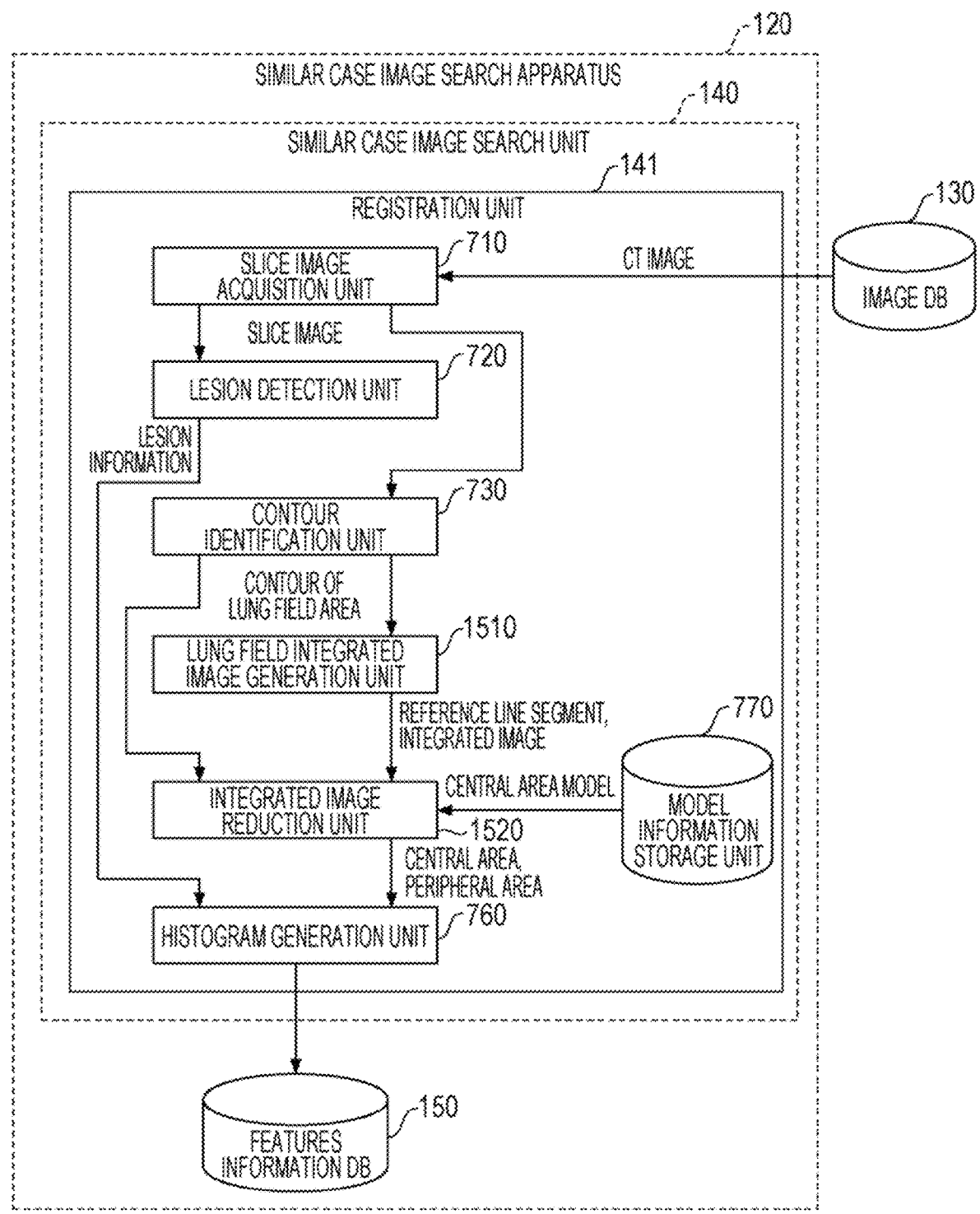
FIG. 15 is a second view illustrating an example of the functional configuration of the registration unit of the similar case image search apparatus.

First, the functional configuration of a registration unit 141 of a similar case image search apparatus 120 in accordance with the second embodiment will be described. FIG. 15 is a second view illustrating an example of the functional configuration of the registration unit of the similar case image search apparatus. The difference between the functional configuration and the functional configuration illustrated in FIG. 7 is that the registration unit 141 has a lung field integrated image generation unit 1510 and an integrated image reduction unit 1520.

The lung field integrated image generation unit 1510 executes integrated image generation processing. Specifically, the lung field integrated Image generation unit 1510 calculates a reference line segment including the chest wall and the mediastinum as endpoints, based on the contours of the lung field areas of the left and right lungs in each slice image, which are notified from the contour identification unit 730. The lung field integrated image generation unit 1510 generates an image formed by integrating the both lung field areas (integrated image), based on the contours of the lung field areas of the left and right lungs in each slice image, which are notified from the contour identification unit 730. Further, the lung field integrated image generation unit 1510 notifies the calculated reference line segment and the generated integrated image to the Integrated image reduction unit 1520.

The integrated image reduction unit 1520 is an example of a division unit, and executes the integrated image reduction processing. Specifically, the integrated image reduction unit 1520 reduces the integrated image notified from the lung field integrated image generation unit 1510, and internally divides the reference line segment in a prescribed proportion to divide the lung field area into the central area and the peripheral area. The integrated image reduction unit 1520 determines the proportion in which the reference line segment is Internally divided based on the central area model acquired from the model information storage unit 770, and identifies the division point based on the determined proportion.

The integrated image reduction unit 1520 notifies the divided central area and peripheral area to the histogram generation unit 760.

<Specific Examples of Processing of Registration Unit of Similar Case Image Search Apparatus>

Next, a specific example of processing of the registration unit 141 of the similar case image search apparatus 120 will be described.

Figure 16A:
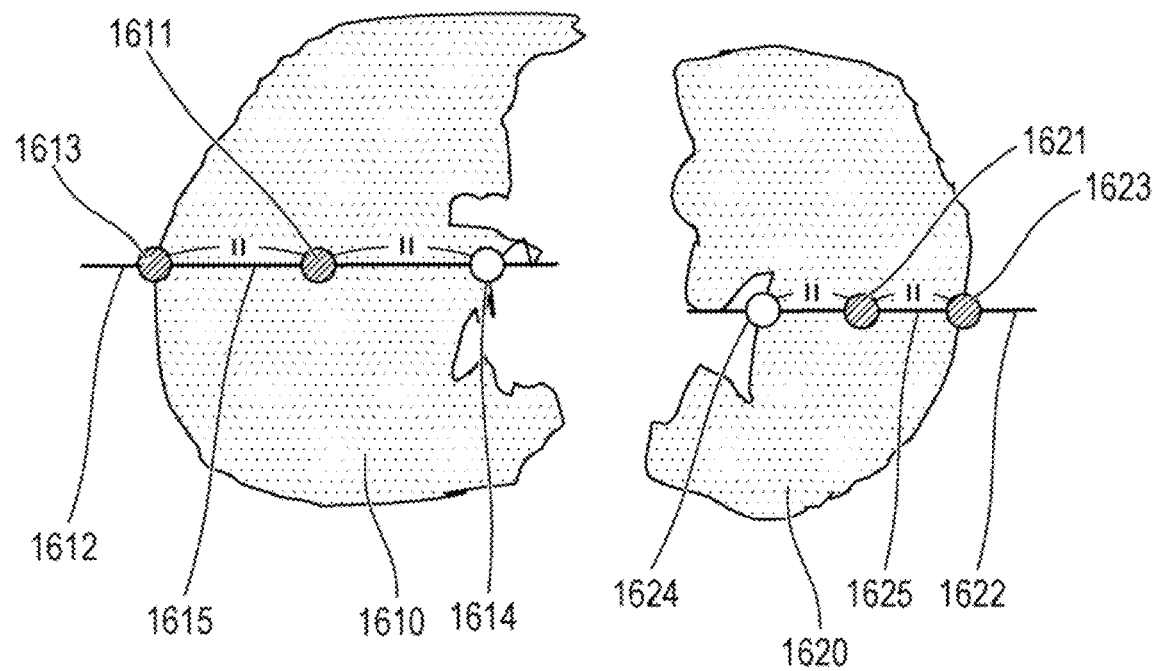
FIGS. 16A and 16B are views illustrating a specific example of Integrated image generation processing of a lung field integrated image generation unit.
Figure 16B:
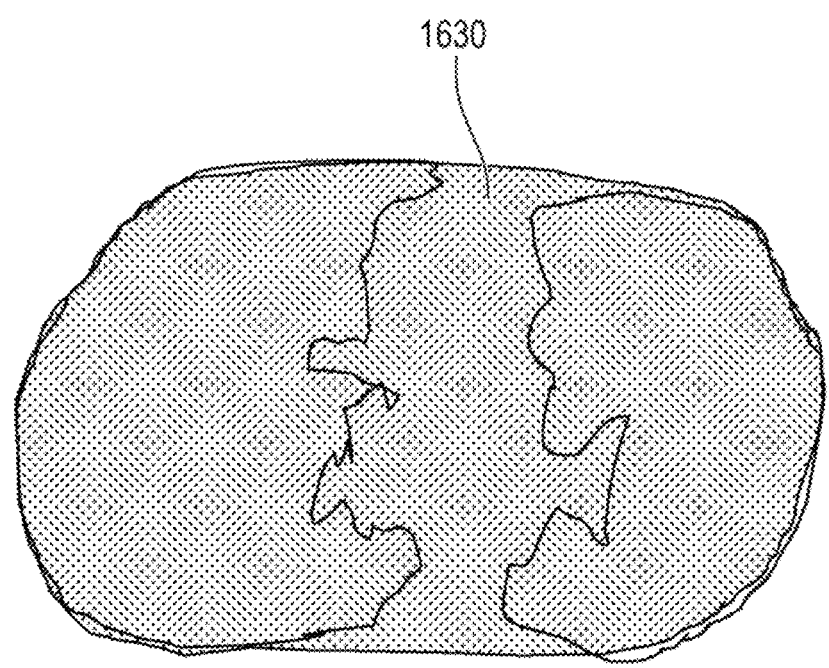

(1) Specific Example of Integrated Image Generation Processing of Lung Field Integrated Image Generation Unit First, a specific example of integrated image generation processing of the lung field integrated image generation unit 1510 of the registration unit 141 will be described. FIGS. 16A and 16B are views illustrating the specific example of the integrated image generation processing of the lung field integrated image generation unit. FIGS. 16A and 16B illustrate the case where a reference line segment for the slice image at the slice position 1033 is calculated to generate an integrated image.

As Illustrated in FIG. 16A, the lung field integrated image generation unit 1510 calculates centroid positions 1611, 1621 of lung field areas 1610, 1620 based on the contours notified from the contour identification unit 730. Subsequently, the lung field integrated image generation unit 1510 calculates a horizontal line 1612 passing the calculated centroid position 1611 and a horizontal line 1622 passing the calculated centroid position 1621.

Subsequently, the lung field integrated image generation unit 1510 extracts an intersection 1613 between the horizontal line 1612 and the outer contour (chest wall) of the lung field area 1610 and an Intersection 1623 between the horizontal line 1622 and the outer contour (chest wall) of the lung field area 1620.

Subsequently, the lung field integrated image generation unit 1510 extracts a point 1614 on the horizontal line 1612, which is located on the opposite side to the Intersection 1613 across the centroid position 1611 away from the centroid position 1611 with the same distance as the distance between the intersection 1613 and the centroid position 1611. Similarly, the lung field integrated image generation unit 1510 extracts a point 1624 on the horizontal line 1622, which is located on the opposite side to the intersection 1623 across the centroid position 1621 away from the centroid position 1621 with the same distance as the distance between the intersection 1623 and the centroid position 1621.

The processing of the lung field integrated image generation unit 1510 is processing of extracting the mediastinum by using the fact that the distance between the chest wall and the centroid position of the lung field area is anatomically equal to the distance between the centroid position of the lung field area and the mediastinum.

Thus, the lung field integrated image generation unit 1510 may calculate reference line segments 1615, 1625 having the chest wall (the Intersection 1613, 1623) and the mediastinum (the points 1614, 1624) as endpoints.

As Illustrated in FIG. 16B, the lung field integrated image generation unit 1510 generates an integrated image 1630 formed by integrating the lung field areas 1610, 1620 based on the shape of the contours (chest wall) of the lung field area 1610, 1620. The lung field integrated image generation unit 1510 notifies the generated integrated image 1630 and the reference line segments 1615, 1625 to the integrated image reduction unit 1520.

Figure 17A:
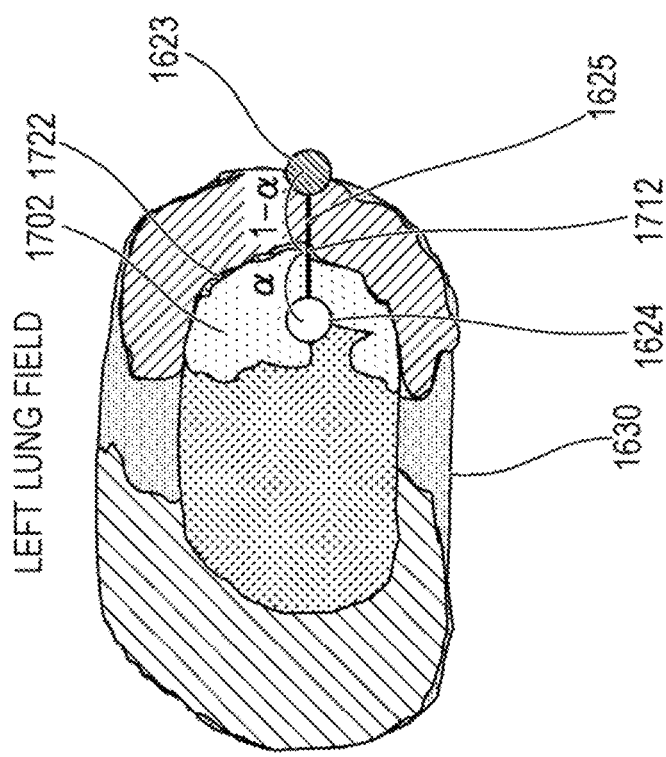
FIGS. 17A and 17B are views illustrating a specific example of integrated image reduction processing of an integrated image reduction unit.
Figure 17B:
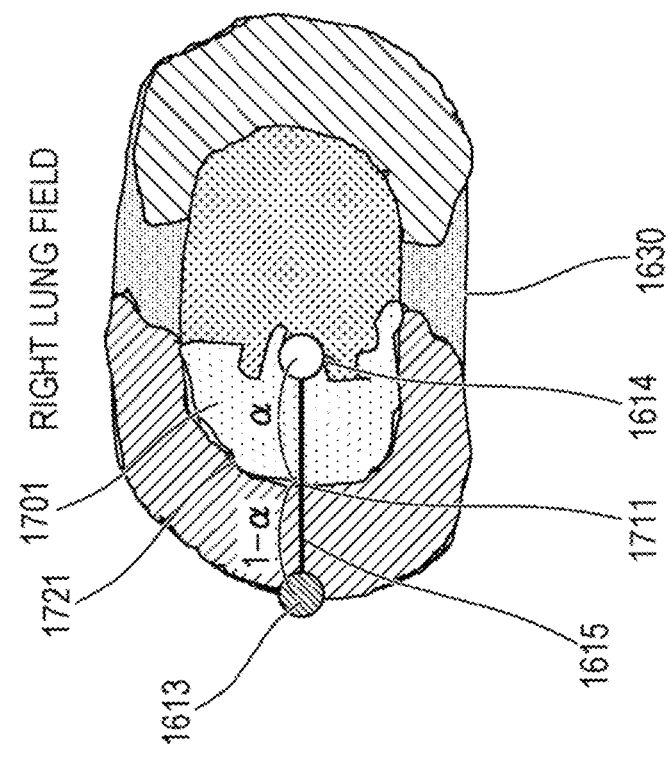

(2) Specific Example of Integrated Image Reduction Processing of Integrated Image Reduction Unit Next, a specific example of integrated image reduction processing of the integrated image reduction unit 1520 of the registration unit 141 will be described. FIGS. 17A and 17B are views illustrating the specific example of the integrated image reduction processing of the integrated image reduction unit.

As illustrated in FIG. 17A, the integrated image reduction unit 1520 reduces the size of the Integrated image 1630 notified from the lung field integrated image generation unit 1510, and generates a reduced integrated image 1701. The integrated image reduction unit 1520 generates the reduced integrated image 1701 such that an intersection 1711 between the reduced integrated image 1701 and the reference line segment 1615 (that is, between the chest wall and the mediastinum) becomes a division point at which the reference line segment 1615 is internally divided in a proportion of $\alpha:(1-\alpha)$.

Thus, the integrated image reduction unit 1520 may calculate a boundary 1721 of the central area in the lung field area of the right lung. The integrated image reduction unit 1520 notifies the inner side of the boundary 1721 of the central area as the central area, and the outer side of the boundary 1721 of the central area as the peripheral area to the histogram generation unit 760.

Similarly, as illustrated in FIG. 17B, the integrated image reduction unit 1520 reduces the size of the integrated image 1630 notified from the lung field integrated image generation unit 1510, and generates a reduced integrated image 1702. The integrated image reduction unit 1520 generates the reduced integrated image 1702 such that an intersection 1712 between the reduced integrated image 1702 and the reference line segment 1625 (that is, between the chest wall and the mediastinum) becomes a division point at which the reference line segment 1625 is internally divided in a proportion of $\alpha:(1-\alpha)$.

Thus, the integrated image reduction unit 1520 may calculate a boundary 1722 of the central area in the lung field area of the left lung. The integrated image reduction unit 1520 notifies the inner side of the boundary 1722 of the central area as the central area, and the outer side of the boundary 1722 of the central area as the peripheral area to the histogram generation unit 760.

As apparent from the above description, in the second embodiment, in each lung field area of each slice image, one point on each of the chest wall and the mediastinum is extracted to calculate the reference line segment, and the size of the integrated image is reduced so as to internally divide the reference line segment in a proportion based on medical findings. In the second embodiment, the boundary of the central area is calculated based on the reduced integrated image to divide the lung field area into the central area and the peripheral area. For this reason, in the second embodiment, the lung field area may be divided into areas suitable for diagnosis.

In the second embodiment, to extract the mediastinum, the contour of the boundary of the lung field area on the side of the chest wall, and the centroid position of the lung field area are used without using the contour of the boundary of the lung field area on the side of the mediastinum, which is difficult to accurately extract the mediastinum. For this reason, in the second embodiment, the accuracy of calculation of the boundary of the central area may be improved, properly dividing the lung field area into the central area and the peripheral area.

Third Embodiment

In the above-mentioned first and second embodiments, the lung field area is divided into the central area and the peripheral area. However, the number of divided areas of the lung field area is not limited to two, and the central area and the peripheral area may be subdivided. This may count the number of lesion pixels of detected lesions in each of the subdivided areas.

FIG. 18 is a second view illustrating an example of the features information stored in the features information DB. A difference between FIG. 18 and FIG. 5A is that, in the features information 1800, each of the right lung field and the left lung field are divided into three or more areas, and the number of lesion pixels of lesions counted in each of the areas is stored.

In this manner, the lung field area is divided into a plurality of areas, and histograms are generated based on the number of lesion pixels counted in each of the areas, thereby improving the accuracy of search for the similar case.

Other Embodiments

The above-mentioned second embodiment fails to mention the functional configuration of the search unit. However, as in the first embodiment, the search unit second embodiment is implemented by adding the similarity level calculation unit 1270 and the output unit 1280 to the registration unit (FIG. 15).

In the above-mentioned embodiments, the histograms are generated to calculate similarity level. However, the method of calculating the similarity level is not limited to this, and may be any method of calculating the similarity level by using the number of lesion pixels in each area.

In the above-mentioned embodiments, the features information 500 and the CT image information 600 are stored in different DBs. However, the features information 500 and the CT image information 600 may be stored in the same DB.

In the above-mentioned embodiments, the histograms for the CT image of the diagnosis subject are generated after acceptance of the search Instruction. However, the histograms for the CT image of the diagnosis subject may be generated before acceptance of the search instruction.

In the above-mentioned embodiments, the CT image is searched as the medical image. However, medical images other than the CT Image (for example, magnetic resonance imaging (MRI) image) may be searched.

The present disclosure is not limited to the configuration described herein, and may be any combination of the configuration in the embodiments described above and other constituents. In this connection, such embodiments may be modified within the scope of the subject matter of the present disclosure, and may be properly adapted to practical applications.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A non-transitory computer-readable storage medium having stored a similar case image search program causing a computer to execute a process comprising:
   extracting a lung field area from a medical image and identifying a contour of the lung field area including a chest wall and a mediastinum;
   identifying a position at which the chest wall and the mediastinum are internally divided and dividing the lung field area into a central area and a peripheral area based on a shape of the lung field area;
   counting the number of pixels indicating lesions in each of the divided central area and peripheral area; and
   identifying a similar case image corresponding to similarity level of the number of pixels indicating lesions by referring to a storage unit that stores the number of pixels indicating lesions in each of the areas,
   wherein in the identifying the position, an intersection between a horizontal line passing a centroid position of the lung field area and the identified contour of the lung field area is extracted as the chest wall, and a point on the horizontal line, which is located on an opposite side to the chest wall across the centroid position away from the centroid position with the same distance as a distance between the chest wall and the centroid position, is extracted as the mediastinum.

2. The storage medium according to claim 1, wherein
for each of a plurality of slice images included in the medical image, a histogram is generated based on the counted number of pixels indicating lesions at each slice position, and
identifying a similar case image corresponding to similarity level of the generated histogram in each of the areas by referring to the storage unit that stores the histogram in each of the areas.

3. The storage medium according to claim 1, wherein
for each of the plurality of slice images included in the medical image, a position at which the chest wall and the mediastinum are internally divided in each of the plurality of slice images included in the medical image is identified by referring to a model defining a proportion in which the chest wall and the mediastinum are internally divided.

4. The storage medium according to claim 1, wherein
for each of the plurality of slice images included in the medical image, a central position of a body is extracted, and intersections between a plurality of straight lines radially extending from the central position and a contour of the identified lung field area are extracted as the chest wall or the mediastinum.

5. The storage medium according to claim 4, wherein
for each of the plurality of slice images included in the medical image, a division curve connecting the plurality of positions at which the chest wall and the mediastinum are internally divided is generated, and the lung field area is divided into a central area and a peripheral area.

6. The storage medium according to claim 1, wherein
for each of the plurality of slice images included in the medical image, an integrated image formed by integrating the two lung field areas is generated, the generated integrated image is reduced so as to pass a position at which the chest wall and the mediastinum are internally divided, and based on the reduced integrated image, the lung field area is divided into a central area and a peripheral area.

7. A similar case image search apparatus comprising:
a memory, and
a processor coupled to the memory and configured to:
extract a lung field area from a medical image and identify a contour of the lung field area including a chest wall and a mediastinum;
identify a position at which the chest wall and the mediastinum are internally divided and divide the lung field area into a central area and a peripheral area based on a shape of the lung field area;
count the number of pixels indicating lesions in each of the divided central area and peripheral area; and
identify a similar case image corresponding to similarity level of the number of pixels indicating lesions by referring to a storage unit that stores the number of pixels indicating lesions in each of the areas,
wherein in the identifying, an intersection between a horizontal line passing a centroid position of the lung field area and the identified contour of the lung field area is extracted as the chest wall, and a point on the horizontal line, which is located on an opposite side to the chest wall across the centroid position away from the centroid position with the same distance as a distance between the chest wall and the centroid position, is extracted as the mediastinum.

8. A similar case image search method performed by a computer, the method comprising:
extracting a lung field area from a medical image and identifying a contour of the lung field area including a chest wall and a mediastinum;
identifying a position at which the chest wall and the mediastinum are internally divided and dividing the lung field area into a central area and a peripheral area based on a shape of the lung field area;
counting the number of pixels indicating lesions in each of the divided central area and peripheral area; and
identifying a similar case image corresponding to similarity level of the number of pixels indicating lesions by referring to a storage unit that stores the number of pixels indicating lesions in each of the areas,
wherein in the identifying, an intersection between a horizontal line passing a centroid position of the lung field area and the identified contour of the lung field area is extracted as the chest wall, and a point on the horizontal line, which is located on an opposite side to the chest wall across the centroid position away from the centroid position with the same distance as a distance between the chest wall and the centroid position, is extracted as the mediastinum.

* * * * *